US009737355B2

(12) United States Patent
Yates et al.

(10) Patent No.: US 9,737,355 B2
(45) Date of Patent: Aug. 22, 2017

(54) CONTROLLING IMPEDANCE RISE IN ELECTROSURGICAL MEDICAL DEVICES

(71) Applicant: Ethicon Endo-Surgery, Inc., Cincinnati, OH (US)

(72) Inventors: David C. Yates, West Chester, OH (US); Jeffrey D. Messerly, Cincinnati, OH (US); Mark A. Davison, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 634 days.

(21) Appl. No.: 14/230,349

(22) Filed: Mar. 31, 2014

(65) Prior Publication Data

US 2015/0272657 A1    Oct. 1, 2015

(51) Int. Cl.
*A61B 18/12*    (2006.01)
*A61B 18/00*    (2006.01)
*A61B 18/14*    (2006.01)

(52) U.S. Cl.
CPC ...... *A61B 18/1233* (2013.01); *A61B 18/1206* (2013.01); *A61B 18/148* (2013.01);
(Continued)

(58) Field of Classification Search
CPC ............ A61B 18/1233; A61B 18/1206; A61B 18/1442; A61B 18/1445; A61B 2018/00875; A61B 2018/00666; A61B 2018/00672; A61B 2018/146; A61B 2018/00607; A61B 2018/00702; A61B 2018/00767
(Continued)

(56) References Cited

U.S. PATENT DOCUMENTS 2,366,274 A    1/1945    Luth et al.
2,458,152 A    1/1949    Eakins
(Continued)

FOREIGN PATENT DOCUMENTS

DE    4300307 A1    7/1994
DE    19608716 C1    4/1997
(Continued)

OTHER PUBLICATIONS

International Search Report for Application No. PCT/US2015/018597, dated May 19, 2015 (6 pages).
(Continued)

*Primary Examiner* — Thomas Giuliani

(57) ABSTRACT

Various embodiments are directed to electrosurgical systems for providing an electrosurgical signal to a patient. A control circuit may, for a first application period, apply the electrosurgical signal to first and second electrodes according to a first mode. In the first mode, the control circuit may limit the electrosurgical signal to a first maximum power when the impedance between the first and second electrodes exceeds a first mode threshold. The control circuit may also, for a second application period after the first application period, apply the electrosurgical signal according to a second mode. In the second mode, the control circuit may limit the electrosurgical signal to a second mode maximum power when the impedance between the first and second electrodes exceeds a second mode threshold. The second maximum power may be greater than the first maximum power.

12 Claims, 24 Drawing Sheets

(52) U.S. Cl.
CPC ....... *A61B 18/1445* (2013.01); *A61B 18/1447* (2013.01); *A61B 2018/0063* (2013.01); *A61B 2018/00589* (2013.01); *A61B 2018/00595* (2013.01); *A61B 2018/00672* (2013.01); *A61B 2018/00678* (2013.01); *A61B 2018/00702* (2013.01); *A61B 2018/00767* (2013.01); *A61B 2018/00827* (2013.01); *A61B 2018/00875* (2013.01); *A61B 2018/00892* (2013.01); *A61B 2018/124* (2013.01); *A61B 2018/1455* (2013.01)

(58) Field of Classification Search
USPC .............................. 606/34, 37, 41, 42, 50–52
See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |

(56) References Cited

U.S. PATENT DOCUMENTS

| | | | |
|---|---|---|---|
| 5,817,084 | A | 10/1998 | Jensen |
| 5,817,093 | A | 10/1998 | Williamson, IV et al. |
| 5,827,323 | A | 10/1998 | Klieman |
| 5,836,909 | A | 11/1998 | Cosmescu |
| 5,836,943 | A | 11/1998 | Miller, III |
| 5,836,990 | A | 11/1998 | Li |
| 5,853,412 | A | 12/1998 | Mayenberger |
| 5,876,401 | A | 3/1999 | Schulze et al. |
| 5,878,193 | A | 3/1999 | Wang et al. |
| 5,880,668 | A | 3/1999 | Hall |
| 5,891,142 | A | 4/1999 | Eggers et al. |
| 5,906,625 | A | 5/1999 | Bito et al. |
| 5,910,129 | A | 6/1999 | Koblish et al. |
| 5,921,956 | A | 7/1999 | Grinberg et al. |
| 5,929,846 | A | 7/1999 | Rosenberg et al. |
| 5,984,938 | A | 11/1999 | Yoon |
| 6,003,517 | A | 12/1999 | Sheffield et al. |
| 6,013,052 | A | 1/2000 | Durman et al. |
| 6,024,741 | A | 2/2000 | Williamson, IV et al. |
| 6,024,744 | A | 2/2000 | Kese et al. |
| 6,033,399 | A | 3/2000 | Gines |
| 6,039,734 | A | 3/2000 | Goble |
| 6,050,996 | A | 4/2000 | Schmaltz et al. |
| 6,063,098 | A | 5/2000 | Houser et al. |
| 6,068,629 | A | 5/2000 | Haissaguerre et al. |
| 6,074,389 | A | 6/2000 | Levine et al. |
| 6,091,995 | A | 7/2000 | Ingle et al. |
| 6,099,483 | A | 8/2000 | Palmer et al. |
| 6,099,550 | A | 8/2000 | Yoon |
| H1904 | H | 10/2000 | Yates et al. |
| 6,132,368 | A | 10/2000 | Cooper |
| 6,144,402 | A | 11/2000 | Norsworthy et al. |
| 6,152,923 | A | 11/2000 | Ryan |
| 6,154,198 | A | 11/2000 | Rosenberg |
| 6,162,208 | A | 12/2000 | Hipps |
| 6,174,309 | B1 | 1/2001 | Wrublewski et al. |
| 6,176,857 | B1 | 1/2001 | Ashley |
| 6,190,386 | B1 | 2/2001 | Rydell |
| 6,206,876 | B1 | 3/2001 | Levine et al. |
| 6,228,080 | B1 | 5/2001 | Gines |
| 6,231,565 | B1 | 5/2001 | Tovey et al. |
| 6,259,230 | B1 | 7/2001 | Chou |
| 6,277,117 | B1 | 8/2001 | Tetzlaff et al. |
| 6,292,700 | B1 | 9/2001 | Morrison et al. |
| 6,325,799 | B1 | 12/2001 | Goble |
| 6,340,878 | B1 | 1/2002 | Oglesbee |
| 6,364,888 | B1 | 4/2002 | Niemeyer et al. |
| 6,387,109 | B1 | 5/2002 | Davison et al. |
| 6,391,026 | B1 | 5/2002 | Hung et al. |
| 6,398,779 | B1 | 6/2002 | Buysse et al. |
| H2037 | H | 7/2002 | Yates et al. |
| 6,419,675 | B1 | 7/2002 | Gallo, Sr. |
| 6,430,446 | B1 | 8/2002 | Knowlton |
| 6,443,968 | B1 | 9/2002 | Holthaus et al. |
| 6,458,128 | B1 | 10/2002 | Schulze |
| 6,464,689 | B1 | 10/2002 | Qin et al. |
| 6,464,702 | B2 | 10/2002 | Schulze et al. |
| 6,480,796 | B2 | 11/2002 | Wiener |
| 6,491,690 | B1 | 12/2002 | Goble et al. |
| 6,500,112 | B1 | 12/2002 | Khouri |
| 6,500,176 | B1 | 12/2002 | Truckai et al. |
| 6,503,248 | B1 | 1/2003 | Levine |
| 6,511,480 | B1 | 1/2003 | Tetzlaff et al. |
| 6,514,252 | B2 | 2/2003 | Nezhat et al. |
| 6,517,565 | B1 | 2/2003 | Whitman et al. |
| 6,531,846 | B1 | 3/2003 | Smith |
| 6,533,784 | B2 | 3/2003 | Truckai et al. |
| 6,537,272 | B2 | 3/2003 | Christopherson et al. |
| 6,537,291 | B2 | 3/2003 | Friedman et al. |
| 6,551,309 | B1 | 4/2003 | LePivert |
| 6,554,829 | B2 | 4/2003 | Schulze et al. |
| 6,558,376 | B2 | 5/2003 | Bishop |
| 6,562,037 | B2 | 5/2003 | Paton et al. |
| 6,572,639 | B1 | 6/2003 | Ingle et al. |
| 6,575,969 | B1 | 6/2003 | Rittman, III et al. |
| 6,582,451 | B1 | 6/2003 | Marucci et al. |
| 6,584,360 | B2 | 6/2003 | Francischelli et al. |
| 6,585,735 | B1 | 7/2003 | Lands et al. |
| 6,589,200 | B1 | 7/2003 | Schwemberger et al. |
| 6,602,252 | B2 | 8/2003 | Mollenauer |
| 6,619,529 | B2 | 9/2003 | Green et al. |
| 6,620,161 | B2 | 9/2003 | Schulze et al. |
| 6,622,731 | B2 | 9/2003 | Daniel et al. |
| 6,623,482 | B2 | 9/2003 | Pendekanti et al. |
| 6,635,057 | B2 | 10/2003 | Harano et al. |
| 6,644,532 | B2 | 11/2003 | Green et al. |
| 6,651,669 | B1 | 11/2003 | Burnside |
| 6,656,177 | B2 | 12/2003 | Truckai et al. |
| 6,656,198 | B2 | 12/2003 | Tsonton et al. |
| 6,662,127 | B2 | 12/2003 | Wiener et al. |
| 6,673,248 | B2 | 1/2004 | Chowdhury |
| 6,679,882 | B1 | 1/2004 | Kornerup |
| 6,695,840 | B2 | 2/2004 | Schulze |
| 6,722,552 | B2 | 4/2004 | Fenton, Jr. |
| 6,746,443 | B1 | 6/2004 | Morley et al. |
| 6,752,815 | B2 | 6/2004 | Beaupre |
| 6,770,072 | B1 | 8/2004 | Truckai et al. |
| 6,773,409 | B2 | 8/2004 | Truckai et al. |
| 6,773,435 | B2 | 8/2004 | Schulze et al. |
| 6,775,575 | B2 | 8/2004 | Bommannan et al. |
| 6,783,524 | B2 | 8/2004 | Anderson et al. |
| 6,789,939 | B2 | 9/2004 | Schrödinger et al. |
| 6,796,981 | B2 | 9/2004 | Wham et al. |
| 6,800,085 | B2 | 10/2004 | Selmon et al. |
| 6,802,843 | B2 | 10/2004 | Truckai et al. |
| 6,811,842 | B1 | 11/2004 | Ehrnsperger et al. |
| 6,821,273 | B2 | 11/2004 | Mollenauer |
| 6,835,199 | B2 | 12/2004 | McGuckin, Jr. et al. |
| 6,840,938 | B1 | 1/2005 | Morley et al. |
| 6,860,880 | B2 | 3/2005 | Treat et al. |
| 6,877,647 | B2 | 4/2005 | Ratcliff et al. |
| 6,905,497 | B2 | 6/2005 | Truckai et al. |
| 6,908,463 | B2 | 6/2005 | Treat et al. |
| 6,913,579 | B2 | 7/2005 | Truckai et al. |
| 6,926,716 | B2 | 8/2005 | Baker et al. |
| 6,929,622 | B2 | 8/2005 | Chian |
| 6,929,644 | B2 | 8/2005 | Truckai et al. |
| 6,953,461 | B2 | 10/2005 | McClurken et al. |
| 6,977,495 | B2 | 12/2005 | Donofrio |
| 6,994,709 | B2 | 2/2006 | Iida |
| 7,000,818 | B2 | 2/2006 | Shelton, IV et al. |
| 7,011,657 | B2 | 3/2006 | Truckai et al. |
| 7,041,102 | B2 | 5/2006 | Truckai et al. |
| 7,052,496 | B2 | 5/2006 | Yamauchi |
| 7,055,731 | B2 | 6/2006 | Shelton, IV et al. |
| 7,063,699 | B2 | 6/2006 | Hess et al. |
| 7,066,936 | B2 | 6/2006 | Ryan |
| 7,070,597 | B2 | 7/2006 | Truckai et al. |
| 7,077,853 | B2 | 7/2006 | Kramer et al. |
| 7,083,618 | B2 | 8/2006 | Couture et al. |
| 7,083,619 | B2 | 8/2006 | Truckai et al. |
| 7,087,054 | B2 | 8/2006 | Truckai et al. |
| 7,094,235 | B2 | 8/2006 | Francischelli et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,112,201 | B2 | 9/2006 | Truckai et al. |
| 7,118,570 | B2 | 10/2006 | Tetzlaff et al. |
| 7,125,409 | B2 | 10/2006 | Truckai et al. |
| 7,131,970 | B2 | 11/2006 | Moses et al. |
| 7,137,980 | B2 | 11/2006 | Buysse et al. |
| 7,143,925 | B2 | 12/2006 | Shelton, IV et al. |
| 7,147,138 | B2 | 12/2006 | Shelton, IV |
| 7,156,846 | B2 | 1/2007 | Dycus et al. |
| 7,160,296 | B2 | 1/2007 | Pearson et al. |
| 7,169,146 | B2 | 1/2007 | Truckai et al. |
| 7,169,156 | B2 | 1/2007 | Hart |
| 7,179,271 | B2 | 2/2007 | Friedman et al. |
| 7,186,253 | B2 | 3/2007 | Truckai et al. |
| 7,189,233 | B2 | 3/2007 | Truckai et al. |
| 7,195,631 | B2 | 3/2007 | Dumbauld |
| 7,207,471 | B2 | 4/2007 | Heinrich et al. |
| 7,220,951 | B2 | 5/2007 | Truckai et al. |
| 7,225,964 | B2 | 6/2007 | Mastri et al. |

(56) References Cited

U.S. PATENT DOCUMENTS

| | | |
|---|---|---|
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |

(56) References Cited

U.S. PATENT DOCUMENTS

| | | |
|---|---|---|
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, Ii |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, Iv et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |

(56) References Cited

U.S. PATENT DOCUMENTS

| | | |
|---|---|---|
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1* | 7/2007 | Couture ............. A61B 18/1445 606/39 |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Crompton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1* | 10/2008 | Zarins ................ A61B 18/1206 607/99 |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118176 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |

(56) References Cited

U.S. PATENT DOCUMENTS

| | | |
|---|---|---|
| 2013/0253256 A1 | 9/2013 | Griffith et al. |
| 2013/0253502 A1 | 9/2013 | Aronow et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0180281 A1 | 6/2014 | Rusin |
| 2014/0194875 A1 | 7/2014 | Reschke et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0265347 A1 | 9/2015 | Yates et al. |
| 2015/0272602 A1 | 10/2015 | Boudreaux et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | | |
|---|---|---|---|
| DE | 29623113 U1 | 10/1997 | |
| DE | 20004812 U1 | 9/2000 | |
| DE | 10201569 A1 | 7/2003 | |
| EP | 0340803 B1 | 8/1993 | |
| EP | 0630612 A1 | 12/1994 | |
| EP | 0705571 A1 | 4/1996 | |
| EP | 0557806 B1 | 5/1998 | |
| EP | 0640317 B1 | 9/1999 | |
| EP | 0722696 B1 | 12/2002 | |
| EP | 1293172 B1 | 4/2006 | |
| EP | 0875209 B1 | 5/2006 | |
| EP | 1704824 A1 | 9/2006 | |
| EP | 1749479 A1 | 2/2007 | |
| EP | 1767157 A1 | 3/2007 | |
| EP | 1254637 B1 | 8/2007 | |
| EP | 1878399 A1 | 1/2008 | |
| EP | 1915953 A1 | 4/2008 | |
| EP | 1532933 B1 | 5/2008 | |
| EP | 1707143 B1 | 6/2008 | |
| EP | 1943957 A2 | 7/2008 | |
| EP | 1435852 B1 | 12/2008 | |
| EP | 1849424 B1 | 4/2009 | |
| EP | 2042117 A1 | 4/2009 | |
| EP | 2060238 A1 | 5/2009 | |
| EP | 1810625 B1 | 8/2009 | |
| EP | 2090238 A1 | 8/2009 | |
| EP | 2090256 A2 | 8/2009 | |
| EP | 2092905 A1 | 8/2009 | |
| EP | 2105104 A2 | 9/2009 | |
| EP | 1747761 B1 | 10/2009 | |
| EP | 1769766 B1 | 2/2010 | |
| EP | 2151204 A1 | 2/2010 | |
| EP | 2153791 A1 | 2/2010 | |
| EP | 2243439 A1 | 10/2010 | |
| EP | 1510178 B1 | 6/2011 | |
| EP | 1728475 B1 | 8/2011 | |
| EP | 2353518 A1 | 8/2011 | |
| EP | 1767164 B1 | 1/2013 | |
| EP | 2316359 B1 | 3/2013 | |
| EP | 2578172 A2 * | 4/2013 | ............ A61B 18/12 |
| EP | 2508143 B1 | 2/2014 | |
| GB | 2472216 A | 2/2011 | |
| JP | H08-229050 | 9/1996 | |
| JP | 2008-018226 | 1/2008 | |
| JP | 5714508 B2 | 5/2015 | |
| WO | WO 81/03272 A1 | 11/1981 | |
| WO | WO 93/07817 A1 | 4/1993 | |
| WO | WO 93/22973 A1 | 11/1993 | |
| WO | WO 95/10978 A1 | 4/1995 | |
| WO | WO 96/35382 A1 | 11/1996 | |
| WO | WO 97/10764 A1 | 3/1997 | |
| WO | WO 98/00069 A1 | 1/1998 | |
| WO | WO 98/40020 A1 | 9/1998 | |
| WO | WO 98/57588 A1 | 12/1998 | |
| WO | WO 99/23960 A1 | 5/1999 | |
| WO | WO 99/40861 A1 | 8/1999 | |
| WO | WO 00/24330 A1 | 5/2000 | |
| WO | WO 00/24331 A1 | 5/2000 | |
| WO | WO 00/25691 A1 | 5/2000 | |
| WO | WO 01/28444 A1 | 4/2001 | |
| WO | WO 02/062241 A1 | 8/2002 | |
| WO | WO 02/080797 A1 | 10/2002 | |
| WO | WO 03/001986 A2 | 1/2003 | |
| WO | WO 03/013374 A1 | 2/2003 | |
| WO | WO 03/020339 A2 | 3/2003 | |
| WO | WO 03/028541 A2 | 4/2003 | |
| WO | WO 03/030708 A2 | 4/2003 | |
| WO | WO 03/068046 A2 | 8/2003 | |
| WO | WO 2004/011037 A2 | 2/2004 | |
| WO | WO 2004/032754 A2 | 4/2004 | |
| WO | WO 2004/032762 A1 | 4/2004 | |
| WO | WO 2004/032763 A2 | 4/2004 | |
| WO | WO 2004/078051 A2 | 9/2004 | |
| WO | WO 2004/112618 A2 | 12/2004 | |
| WO | WO 2005/052959 A2 | 6/2005 | |
| WO | WO 2006/021269 A1 | 3/2006 | |
| WO | WO 2006/036706 A1 | 4/2006 | |

(56) References Cited

FOREIGN PATENT DOCUMENTS

| WO | WO 2006/055166 A2 | 5/2006 |
|---|---|---|
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Written Opinion for Application No. PCT/US2015/018597, dated May 19, 2015 (7 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=joumal&source=Ml&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

\* cited by examiner

CONTROLLING IMPEDANCE RISE IN ELECTROSURGICAL MEDICAL DEVICES

BACKGROUND

Electrosurgical instruments are a type of surgical instrument used in many surgical operations. Electrosurgical instruments apply electrical energy to tissue in order to treat tissue. An electrosurgical instrument may comprise an instrument having a distally-mounted end effector comprising one or more electrodes. The end effector can be positioned against tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active (or source) electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical instrument sometimes also comprises a cutting member that is moveable relative to the tissue and the electrodes to transect the tissue.

Electrical energy applied by an electrosurgical instrument can be transmitted to the instrument by a generator. The generator may form an electrosurgical signal that is applied to an electrode or electrodes of the electrosurgical instrument. The generator may be external or integral to the electrosurgical instrument. The electrosurgical signal may be in the form of radio frequency ("RF") energy. For example, RF energy may be provided at a frequency range of between 100 kHz and 1 MHz. During operation, an electrosurgical instrument can transmit RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

During the application of RF energy to tissue, the impedance of the tissue indicates the condition of the tissue. What is needed are methods and systems for managing the impedance of tissue during the application of RF energy to achieve optimal tissue treatment.

SUMMARY

Various embodiments are directed to electrosurgical systems for providing an electrosurgical signal to a patient. A control circuit may, for a first application period, apply the electrosurgical signal to first and second electrodes according to a first mode. In the first mode, the control circuit may limit the electrosurgical signal to a first maximum power when the impedance between the first and second electrodes exceeds a first mode threshold. The control circuit may also, for a second application period after the first application period, apply the electrosurgical signal according to a second mode. In the second mode, the control circuit may limit the electrosurgical signal to a second mode maximum power when the impedance between the first and second electrodes exceeds a second mode threshold. The second maximum power may be greater than the first maximum power.

FIGURES

The features of the various embodiments are set forth with particularity in the appended claims. The various embodiments, however, both as to organization and methods of operation, together with advantages thereof, may best be understood by reference to the following description, taken in conjunction with the accompanying drawings as follows:

DESCRIPTION

Reference will now be made in detail to several embodiments, including embodiments showing example implementations of electrosurgical instruments for cutting and coagulating tissue. Wherever practicable similar or like reference numbers may be used in the figures and may indicate similar or like functionality. The figures depict example embodiments of the disclosed electrosurgical instruments and/or methods of use for purposes of illustration only. One skilled in the art will readily recognize from the following description that alternative example embodiments of the structures and methods illustrated herein may be employed without departing from the principles described herein.

Figure 1:
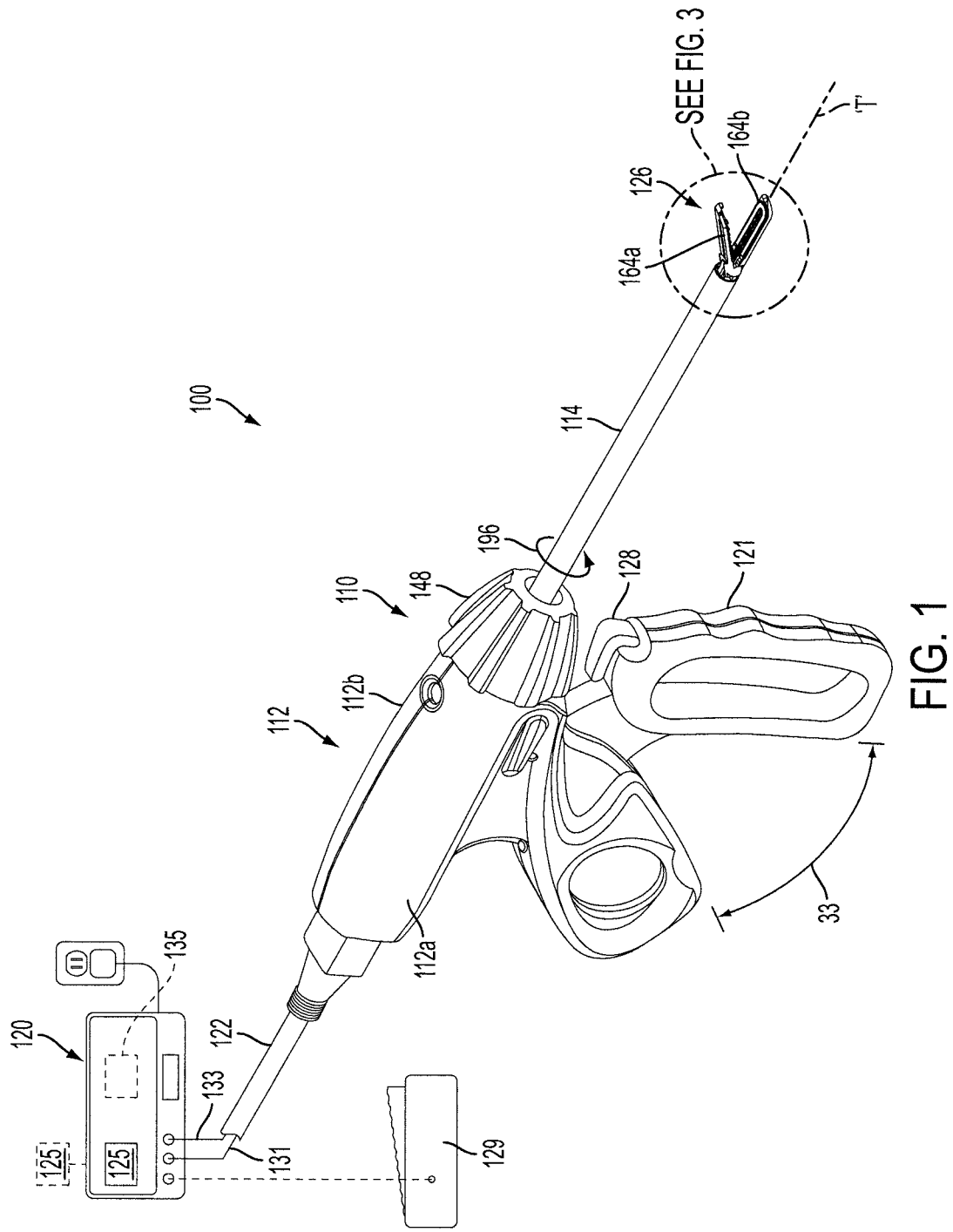
FIG. 1 shows a perspective view of one example embodiment of a surgical system comprising an electrosurgical instrument and an external generator.

Electrosurgical instruments utilize therapeutic and/or sub-therapeutic electrical energy to treat tissue and/or provide feedback to the generators. The various electrosurgical instruments described herein are adapted for use in a manual or hand-operated manner, although electrosurgical instruments with the features described herein may be used in robotic applications as well. FIG. 1 shows a perspective view of one example embodiment of a surgical system 100 comprising an electrosurgical instrument 110 and an external generator 120. The electrosurgical instrument 110 may comprise a proximal handle 112, a distal working end or end effector 126 and an introducer or elongated shaft 114 disposed in-between.

The electrosurgical system 100 can be configured to supply energy, such as electrical energy, ultrasonic energy, heat energy, or any combination thereof, to the tissue of a patient either independently or simultaneously, for example. In one example embodiment, the electrosurgical system 100 includes the generator 120 in electrical communication with the electrosurgical instrument 110. The generator 120 is connected to the electrosurgical instrument 110 via a suitable transmission medium such as a cable 122. In one example embodiment, the generator 120 is coupled to a controller, such as a control unit 125, for example. In various embodiments, the control unit 125 may be formed integrally with the generator 120 or may be provided as a separate circuit module or device electrically coupled to the generator 120 (shown in phantom to illustrate this option). Although in the presently disclosed embodiment, the generator 120 is shown separate from the electrosurgical instrument 110, in one example embodiment, the generator 120 (and/or the control unit 125) may be formed integrally with the electrosurgical instrument 110 to form a unitary electrosurgical system 100, where a battery located within the electrosurgical instrument 110 is the energy source and a circuit coupled to the battery produces the suitable electrical energy, ultrasonic energy, or heat energy. One such example is described herein below in connection with FIGS. 7-8C. The generator 120 may comprise an input device 135 located on a front panel of the generator 120 console. The input device 135 may comprise any suitable device that generates signals suitable for programming the operation of the generator 120, such as a keyboard, or input port, for example.

Referring now to the end effector 126, electrodes in the first jaw 164a and the second jaw 164b may be coupled to the generator 120 via the handle 112 and cable 122. The cable 122 may comprise multiple electrical conductors for the application of electrical energy to positive (+) and negative (−) electrodes of the electrosurgical instrument 110. For example, the cable 122 may comprise at least one supply conductor 131 and at least one return conductor 133. In various embodiments, the supply conductor 131 and the return conductor 133 may comprise insulated wires and/or any other suitable type of conductor. In certain embodiments, as described below, the supply conductor 131 and the return conductor 133 may be contained within and/or may comprise the cable 122 extending between, or at least partially between, the generator 120 and the end effector 126 of the electrosurgical instrument 110. In any event, the generator 120 can be configured to apply a sufficient voltage differential between the supply conductor 131 and the return conductor 133 such that sufficient current can be supplied to the end effector 126.

The control unit 125 may be used to activate the generator 120, which may serve as an electrical source. The generator may create an electrosurgical drive signal provided to the electrodes of the jaws 164a, 164b via the handle 112. In various embodiments, the generator 120 may comprise an RF or electrosurgical source, an ultrasonic source, a direct current source, and/or any other suitable type of electrical energy source, for example, which may be activated independently or simultaneously.

Figure 2:
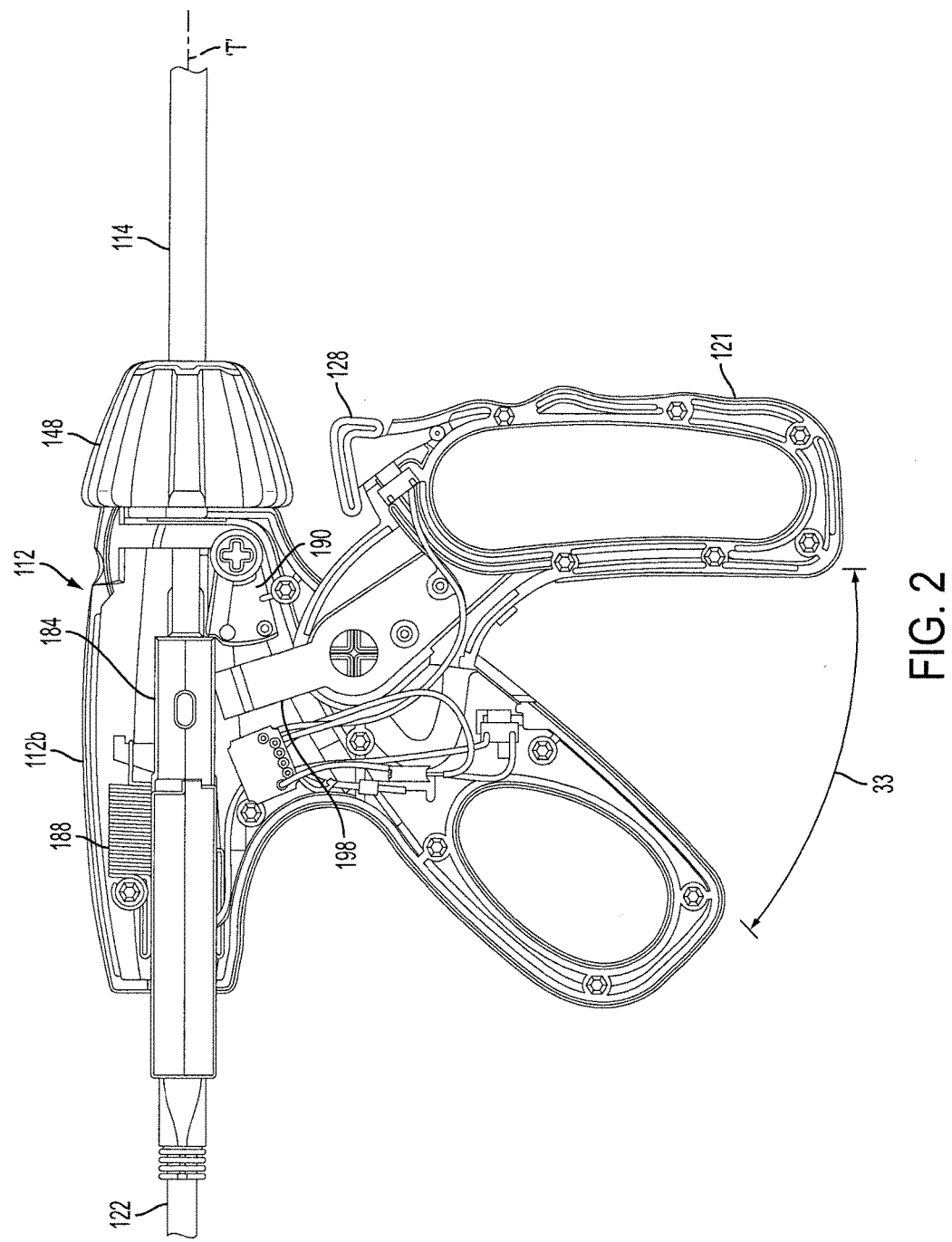
FIG. 2 shows a side view of one example embodiment of the handle of the surgical instrument of FIG. 1 with half of a first handle body removed to illustrate various components within the second handle body.

FIG. 2 shows a side view of one example embodiment of the handle 112 of the surgical instrument 110 with half of a first handle body 112a (see FIG. 1) removed to illustrate various components within the second handle body 112b. The handle 112 may comprise a lever arm 121 (e.g., a trigger) which may be pulled along a path 33. The lever arm 121 may be coupled to an axially moveable member 178 (FIGS. 3-6) disposed within the elongated shaft 114 by a shuttle 184 operably engaged to an extension 198 of lever arm 121. The shuttle 184 may further be connected to a biasing device, such as a spring 188, which may also be connected to the second handle body 112b, to bias the shuttle 184 and thus the axially moveable member 178 in a proximal direction, thereby urging the jaws 164a and 164b to an open position as seen in FIG. 1. Also, referring to FIGS. 1-2, a locking member 190 (see FIG. 2) may be moved by a locking switch between a locked position, where the shuttle 184 is substantially prevented from moving distally as illustrated, and an unlocked position, where the shuttle 184 may be allowed to freely move in the distal direction, toward the elongated shaft 114. The handle 112 can be any type of pistol-grip or other type of handle known in the art that is configured to carry actuator levers, triggers or sliders for actuating the first jaw 164a and the second jaw 164b. In some embodiments, the handle 112 may comprise a pencilstyle handle. The elongated shaft 114 may have a cylindrical or rectangular cross-section, for example, and can comprise a thin-wall tubular sleeve that extends from handle 112. The elongated shaft 114 may include a bore extending therethrough for carrying actuator mechanisms, for example, the axially moveable member 178, for actuating the jaws and for carrying electrical leads for delivery of electrical energy to electrosurgical components of the end effector 126.

The end effector 126 may be adapted for capturing and transecting tissue and for contemporaneously welding the captured tissue with controlled application of energy (e.g., RF energy). The first jaw 164a and the second jaw 164b may close to thereby capture or engage tissue about a longitudinal axis "T" defined by the axially moveable member 178. The first jaw 164a and second jaw 164b may also apply compression to the tissue. In some embodiments, the elongated shaft 114, along with the first jaw 164a and second jaw 164b, can be rotated a full 360° degrees, as shown by the arrow 196 (see FIG. 1), relative to the handle 112. For example, a rotation knob 148 may be rotatable about the longitudinal axis of the shaft 114 and may be coupled to the shaft 114 such that rotation of the knob 148 causes corresponding rotation of the shaft 114. The first jaw 164a and the second jaw 164b can remain openable and/or closeable while rotated.

Figure 3:
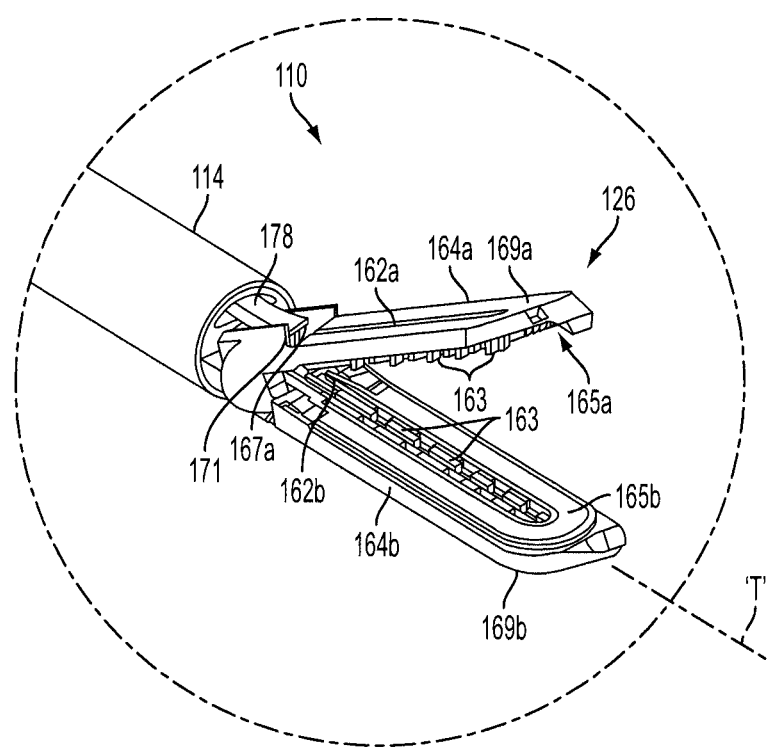
FIG. 3 shows a perspective view of one embodiment of the end effector of the surgical instrument of FIG. 1 with the jaws open and the distal end of an axially moveable member in a retracted position.
Figure 4:
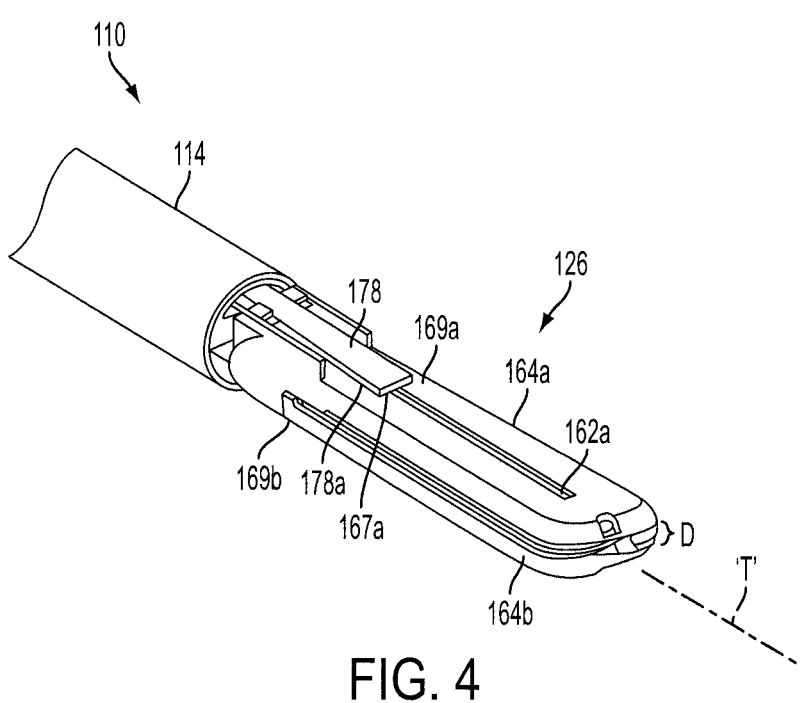
FIG. 4 shows a perspective view of one embodiment of the end effector of the surgical instrument of FIG. 1 with the jaws closed and the distal end of an axially moveable member in a partially advanced position.

FIG. 3 shows a perspective view of one example embodiment of the end effector 126 with the jaws 164a, 164b open and the distal end of the axially moveable member 178 in a retracted position. FIG. 4 shows a perspective view of one embodiment of the end effector 126 with the jaws 164a, 164b closed and the distal end of the axially moveable member 178 in a partially advanced position. As noted above, the end effector 126 may comprise the upper first jaw 164a and the lower second jaw 164b, which may be straight or curved. The first jaw 164a and the second jaw 164b may each comprise an elongated slot or channel 162a and 162b, respectively, disposed outwardly along their respective middle portions. Further, the first jaw 164a and the second jaw 164b may each have tissue-gripping elements, such as teeth 163, disposed on the inner portions of the first jaw 164a and the second jaw 164b. The first jaw 164a may comprise an upper first jaw body with an upper first outward-facing surface 169a and an upper first energy delivery surface 165a. The second jaw 164b may comprise a lower second jaw body with a lower second outward-facing surface 169b and a lower second energy delivery surface 165b. The first energy delivery surface 165a and the second energy delivery surface 165b may both extend in a "U" shape about the distal end of the end effector 126.

Figure 5:
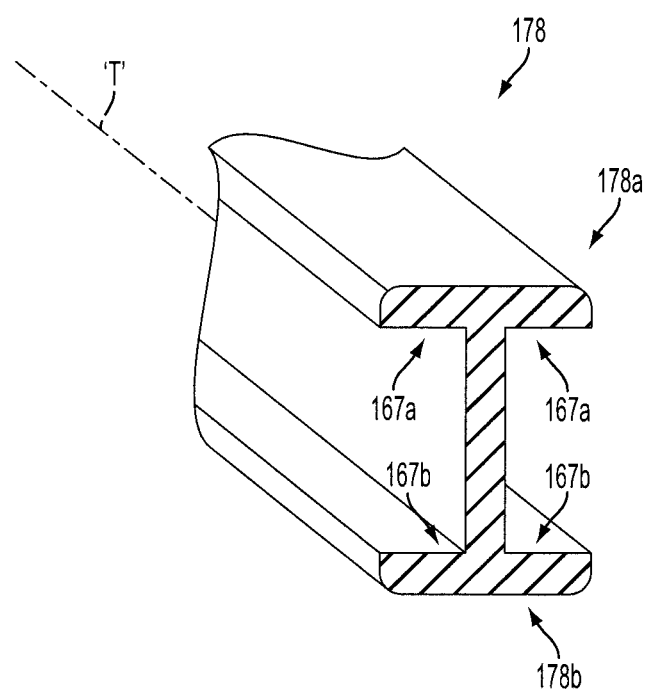
FIG. 5 shows a perspective view of one embodiment of the axially moveable member of the surgical instrument of FIG. 1.

The lever arm 121 of the handle 112 (FIG. 2) may be adapted to actuate the axially moveable member 178, which also may function as a jaw-closing mechanism. For example, the axially moveable member 178 may be urged distally as the lever arm 121 is pulled proximally along the path 33 via the shuttle 184, as shown in FIG. 2 and discussed above. FIG. 5 is a perspective view of one example embodiment of the axially moveable member 178 of the surgical instrument 110. The axially moveable member 178 may comprise one or several pieces, but in any event, may be moveable or translatable with respect to the elongated shaft 114 and/or the jaws 164a, 164b. Also, in at least one example embodiment, the axially moveable member 178 may be made of 17-4 precipitation hardened stainless steel. The distal end of axially moveable member 178 may comprise a flanged "I"-beam configured to slide within the channels 162a and 162b in jaws 164a and 164b. The axially moveable member 178 may slide within the channels 162a, 162b to open and close the first jaw 164a and the second jaw 164b. The distal end of the axially moveable member 178 may also comprise an upper flange or "c"-shaped portion 178a and a lower flange or "c"-shaped portion 178b. The flanges 178a, 178b respectively define inner cam surfaces 167a and 167b for engaging outward facing surfaces of the first jaw 164a and the second jaw 164b. The opening-closing of jaws 164a and 164b can apply very high compressive forces on tissue using cam mechanisms which may include moveable "I-beam" axially moveable member 178 and the outward facing surfaces 169a, 169b of jaws 164a, 164b.

More specifically, referring now to FIGS. 3-5, collectively, the inner cam surfaces 167a and 167b of the distal end of axially moveable member 178 may be adapted to slidably engage the first outward-facing surface 369a and the second outward-facing surface 169b of the first jaw 164a and the second jaw 164b, respectively. The channel 162a within first jaw 164a and the channel 162b within the second jaw 164b may be sized and configured to accommodate the movement of the axially moveable member 178, which may comprise a tissue-cutting element 171, for example, comprising a sharp distal edge. FIG. 4, for example, shows the distal end of the axially moveable member 178 advanced at least partially through channels 162a and 162b (FIG. 3). The advancement of the axially moveable member 178 may close the end effector 126 from the open configuration shown in FIG. 3. In the closed position shown by FIG. 4, the upper first jaw 164a and the lower second jaw 164b define a gap or dimension D between the first energy delivery surface 165a and second energy delivery surface 165b of the first jaw 164a and the second jaw 164b, respectively. In various embodiments, dimension the D can equal from about 0.0005" to about 0.040", for example, and in some embodiments, between about 0.001" to about 0.010", for example. Also, the edges of the first energy delivery surface 165a and the second energy delivery surface 165b may be rounded to prevent the dissection of tissue.

Figure 6:
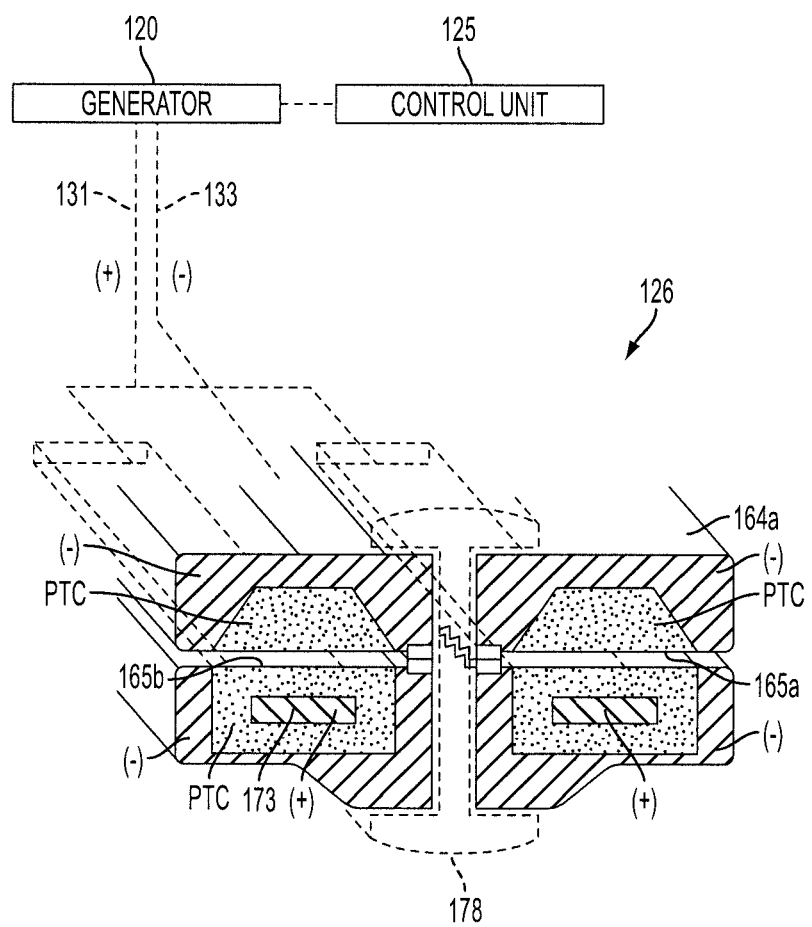
FIG. 6 shows a section view of one embodiment of the end effector of the surgical instrument of FIG. 1.

FIG. 6 is a section view of one example embodiment of the end effector 126 of the surgical instrument 110. The second energy delivery surface 165b of the lower jaw 164b is adapted to deliver energy to tissue, at least in part, through a conductive-resistive matrix, such as a variable resistive PTC body, as discussed in more detail below. At least one of the upper and lower jaws 164a, 164b may carry at least one electrode 173 configured to deliver the energy from the generator 120 to the captured tissue. The the first energy delivery surface 165a of the upper jaw 164a may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 165a and the second energy delivery surface 165b each may be in electrical communication with the generator 120. The first energy delivery surface 165a and the second energy delivery surface 165b may be configured to contact tissue and deliver electrosurgical energy to captured tissue to seal or weld the tissue. The control unit 125 regulates the electrical energy delivered by electrical generator 120 which in turn delivers electrosurgical energy to the first energy delivery surface 165a and the second energy delivery surface 165b. The energy delivery may be initiated by an activation button 128

(FIG. 2) operably engaged with the lever arm 121 and in electrical communication with the generator 120 via a cable 122. In one example embodiment, the electrosurgical instrument 110 may be energized by the generator 120 by way of a foot switch 129 (FIG. 1). When actuated, the foot switch 129 triggers the generator 120 to deliver electrical energy to the end effector 126, for example. The control unit 125 may regulate the power generated by the generator 120 during activation. Although the foot switch 129 may be suitable in many circumstances, other suitable types of switches can be used, such as, for example, a thumb switch.

As mentioned above, the electrosurgical energy delivered by electrical generator 120 and regulated, or otherwise controlled, by the control unit 125 may comprise radio frequency (RF) energy, or other suitable forms of electrical energy. Further, the opposing first and second energy delivery surfaces 165a and 165b may carry variable resistive PTC bodies that are in electrical communication with the generator 120 and the control unit 125. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; and 6,533,784; and U.S. Pat. App. Pub. Nos. 2010/0036370 and 2009/0076506, all of which are incorporated herein by reference in their entirety and made part of this specification.

In one example embodiment, the generator 120 may be implemented as an electrosurgery unit (ESU) capable of supplying power sufficient to perform bipolar electrosurgery using radio frequency (RF) energy. In one example embodiment, the ESU can be a bipolar ERBE VIO 150 sold by ERBE USA, Inc. of Marietta, Ga. and/or a GEN11 generator sold by Ethicon Endo-Surgery of Cincinnati, Ohio. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the PTC bodies and to the return electrode through the tissue. Thus, in various embodiments, the electrosurgical system 100 may comprise a supply path and a return path, where the captured tissue being treated completes, or closes, the circuit. In some embodiments, the operator may provide subtherapeutic RF energy levels for purposes of evaluating tissue conditions and providing feedback in the electrosurgical system 100. Such feed back may be employed to control the therapeutic RF energy output of the electrosurgical instrument 110.

During operation of electrosurgical instrument 110, the user generally grasps tissue, supplies energy to the grasped tissue to form a weld or a seal (e.g., by actuating button 128 and/or foot switch 129), and then drives a tissue-cutting element 171 at the distal end of the axially moveable member 178 through the grasped tissue. According to various embodiments, the translation of the axial movement of the axially moveable member 178 may be paced, or otherwise controlled, to aid in driving the axially moveable member 178 at a suitable rate of travel. By controlling the rate of the travel, the likelihood that the captured tissue has been properly and functionally sealed prior to transection with the cutting element 171 is increased.

Figure 7:
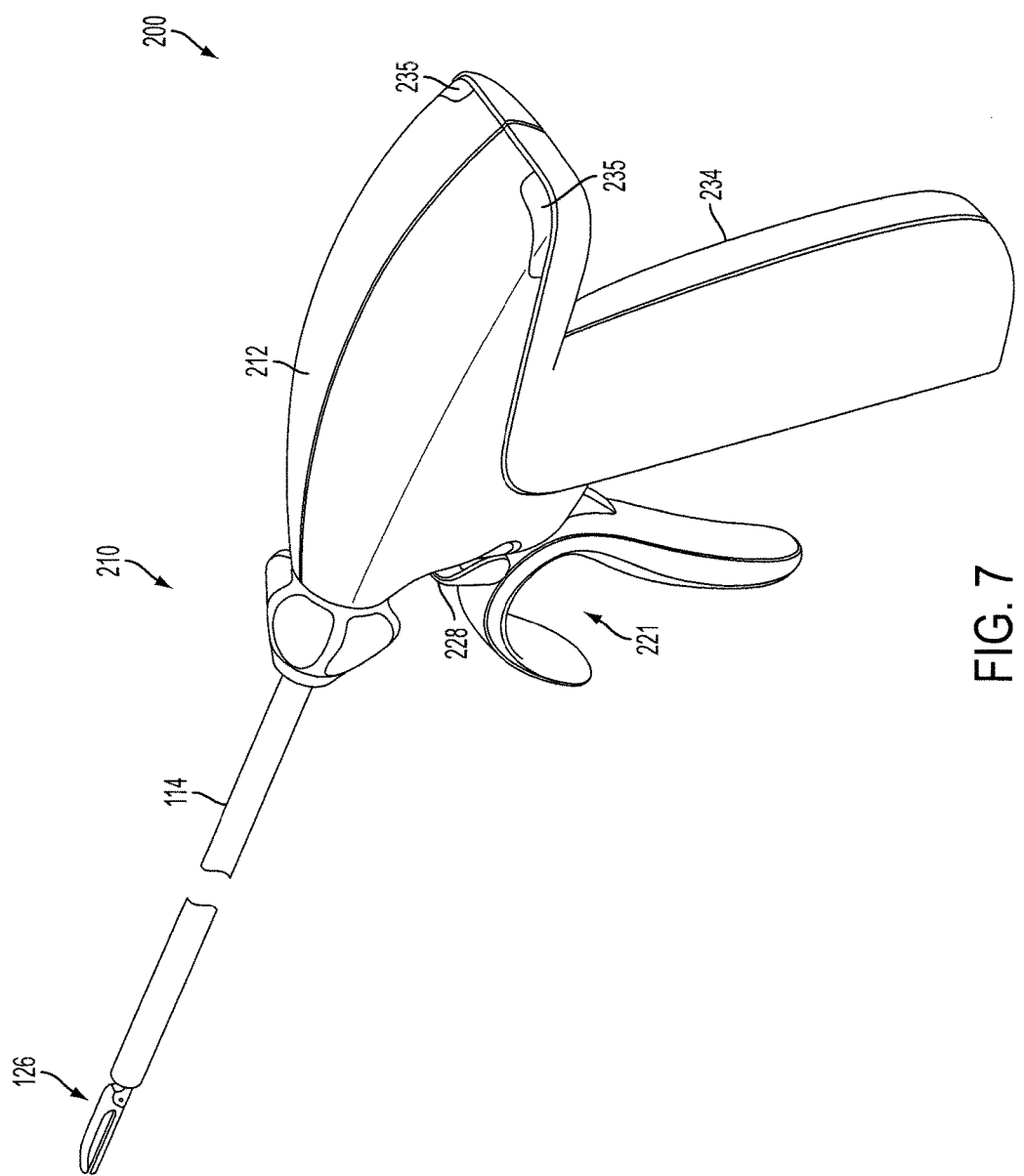
FIG. 7 shows a perspective view of one example embodiment of a surgical system comprising a cordless electrical energy surgical instrument with an integral generator.

FIG. 7 shows a perspective view of one example embodiment of a surgical system 200 comprising a cordless electrical energy surgical instrument 210 with an integral generator (not shown in FIG. 7). The electrosurgical system 200 is similar to the electrosurgical system 100. The electrosurgical system 200 can be configured to supply energy, such as electrical energy, ultrasonic energy, heat energy, or any combination thereof, to the tissue of a patient either independently or simultaneously as described in connection with FIG. 1, for example. The electrosurgical instrument 210 may utilize the end effector 126 and elongated shaft 114 described here in conjunction with a cordless proximal handle 212. In one example embodiment, the handle 212 includes the integral generator circuit 220 (see FIG. 8A). The generator circuit 220 performs a function substantially similar to that of generator 120. In one example embodiment, the generator circuit 220 is coupled to a controller or control circuit (e.g., 281 in FIG. 8B). In the illustrated embodiment, the control circuit is integrated into the generator circuit 220. In other embodiments, the control circuit may be separate from the generator circuit 220.

In one example embodiment, various electrodes in the end effector 126 (including the first and second jaws 164a, 164b thereof) may be coupled to the generator circuit 220. The control circuit may be used to activate the generator 220, which may serve as an electrical source. In various embodiments, the generator 220 may comprise an RF source, an ultrasonic source, a direct current source, a microwave source, and/or any other suitable type of thermogenic energy source, for example. For example, a direct current source may be utilized to power a heating element that could treat tissue. In one example embodiment, a button 228 may be provided to activate the generator circuit 220 to provide energy to the end effector 126.

Figure 8A:
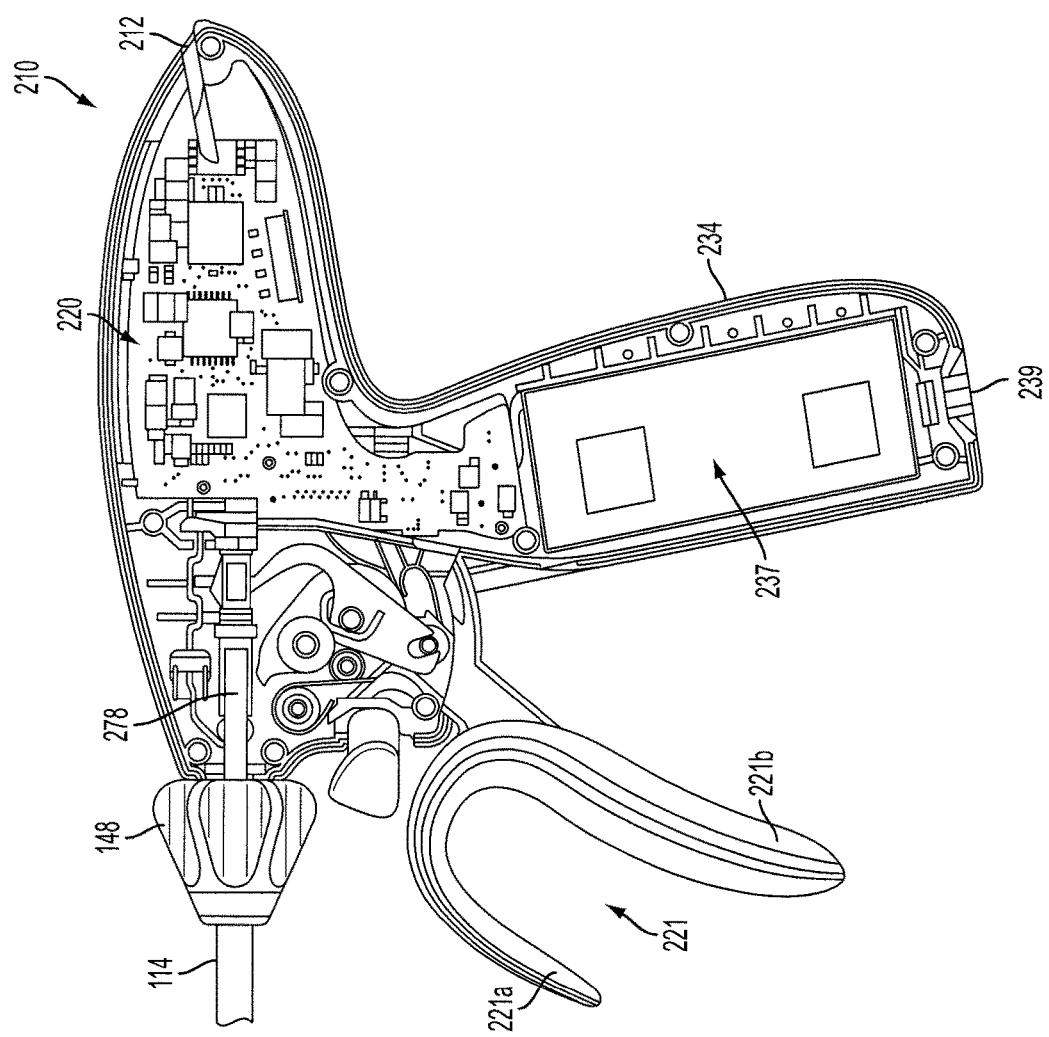
FIG. 8A shows a side view of a handle of one embodiment of the surgical instrument of FIG. 7 with half of the handle body removed to illustrate various components therein.

FIG. 8A shows a side view of one example embodiment of the handle 212 of the cordless surgical instrument 210 with half of a first handle body removed to illustrate various components within the second handle body 234. The handle 212 may comprise a lever arm 221 (e.g., a trigger) which may be pulled along a path 33 around a pivot point. The lever arm 221 may be coupled to an axially moveable member 278 disposed within the elongated shaft 114 by a shuttle operably engaged to an extension of lever arm 221. In one example embodiment, the lever arm 221 defines a shepherd's hook shape comprising a distal trigger hook 221a and a proximal trigger portion 221b. As illustrated, the distal trigger hook 221a may have a first length while the proximal trigger portion 221b may have a second length with the second length greater than the first length.

In one example embodiment, the cordless electrosurgical instrument comprises a battery 237. The battery 237 provides electrical energy to the generator circuit 220. The battery 237 may be any battery suitable for driving the generator circuit 220 at the desired energy levels. In one example embodiment, the battery 237 is a 1030 mAhr, triple-cell Lithium Ion Polymer battery. The battery may be fully charged prior to use in a surgical procedure, and may hold a voltage of about 12.6V. The battery 237 may have two fuses fitted to the cordless electrosurgical instrument 210, arranged in line with each battery terminal. In one example embodiment, a charging port 239 is provided to connect the battery 237 to a DC current source (not shown).

Figure 8B:
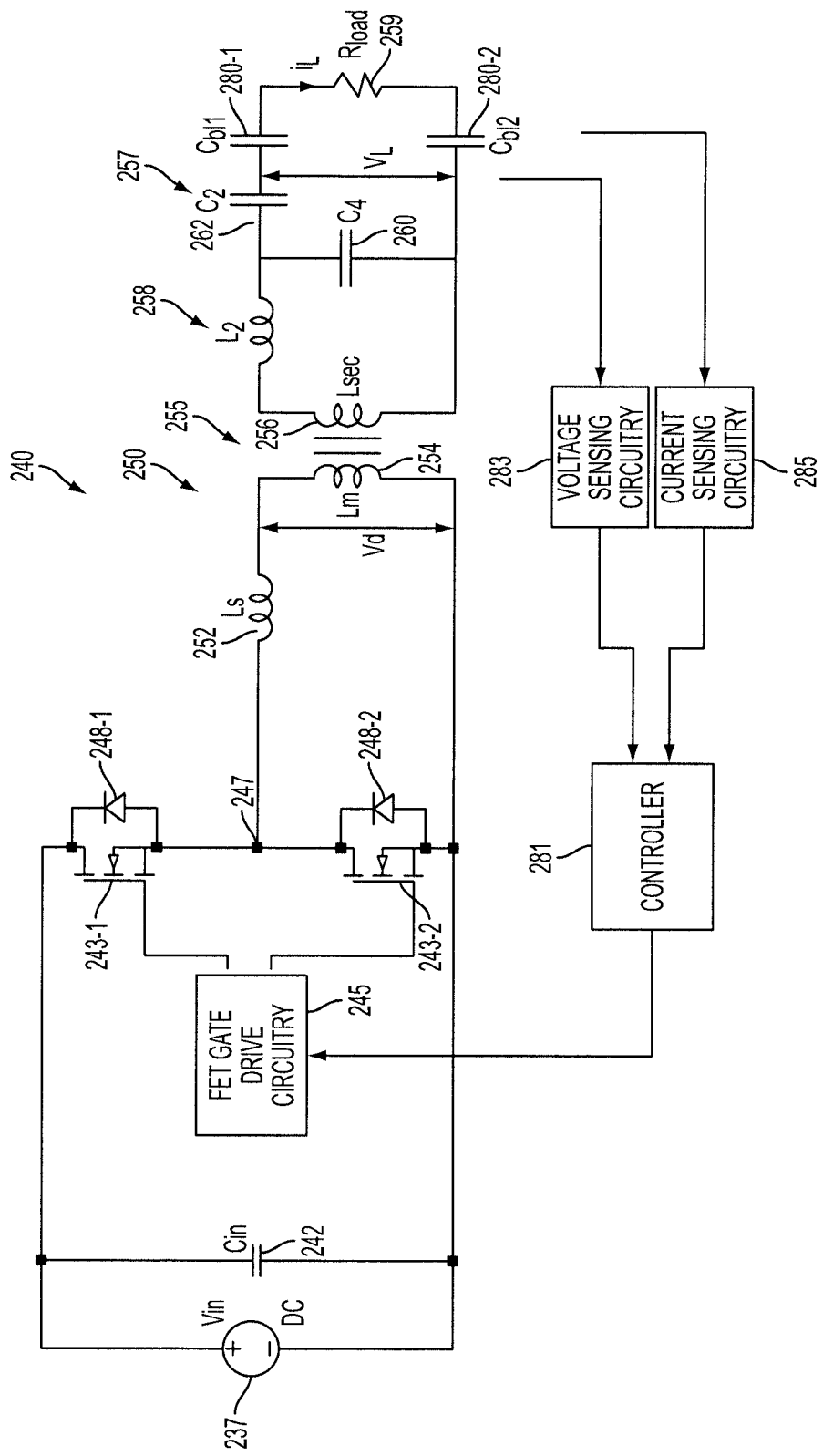
FIG. 8B shows one embodiment of an RF drive and control circuit.

The generator circuit 220 may be configured in any suitable manner. In some embodiments, the generator circuit comprises an RF drive and control circuit 240 and a controller circuit 282. FIG. 8B shows one embodiment of an RF drive and control circuit 240. FIG. 8B is a part schematic part block diagram showing the RF drive and control circuitry 240 used in this embodiment to generate and control the RF electrical energy supplied to the end effector 126. In this embodiment, the drive circuitry 240 is a resonant mode RF amplifier comprising a parallel resonant network on the RF amplifier output and the control circuitry operates to control the operating frequency of the electrosurgical drive signal so that it is maintained at the resonant frequency of the drive circuit, which in turn controls the amount of power supplied to the end effector 126. The way that this is achieved will become apparent from the following description.

As shown in FIG. 8B, the RF drive and control circuit 240 comprises the above described battery 237 are arranged to supply, in this example, about 0V and about 12V rails. An input capacitor ($C_{in}$) 242 is connected between the 0V and the 12V for providing a low source impedance. A pair of FET switches 243-1 and 243-2 (both of which are N-channel in this embodiment to reduce power losses) is connected in series between the 0V rail and the 12V rail. FET gate drive circuitry 245 is provided that generates two drive signals—one for driving each of the two FET's 243. The FET gate drive circuitry 245 generates drive signals that causes the upper FET (243-1) to be on when the lower FET (243-2) is off and vice versa. This causes the node 247 to be alternately connected to the 12V rail (when the FET 243-1 is switched on) and the 0V rail (when the FET 243-2 is switched on). FIG. 8B also shows the internal parasitic diodes 248-1 and 248-2 of the corresponding FET's 243, which conduct during any periods that the FET's 243 are open.

As shown in FIG. 8B, the node 247 is connected to an inductor-inductor resonant circuit 250 formed by inductor $L_s$ 252 and inductor $L_m$ 254. The FET gate driving circuitry 245 is arranged to generate drive signals at a drive frequency ($f_d$) that opens and crosses the FET switches 243 at the resonant frequency of the parallel resonant circuit 250. As a result of the resonant characteristic of the resonant circuit 250, the square wave voltage at node 247 will cause a substantially sinusoidal current at the drive frequency ($f_d$) to flow within the resonant circuit 250. As illustrated in FIG. 8B, the inductor $L_m$ 254 is the primary of a transformer 255, the secondary of which is formed by inductor $L_{sec}$ 256. The inductor $L_{sec}$ 256 of the transformer 255 secondary is connected to an inductor-capacitor-capacitor parallel resonant circuit 257 formed by inductor $L_2$ 258, capacitor $C_4$ 260, and capacitor $C_2$ 262. The transformer 255 up-converts the drive voltage ($V_d$) across the inductor $L_m$ 254 to the voltage that is applied to the output parallel resonant circuit 257. The load voltage ($V_L$) is output by the parallel resonant circuit 257 and is applied to the load (represented by the load resistance $R_{load}$ 259 in FIG. 8B) corresponding to the impedance of the forceps' jaws and any tissue or vessel gripped by the end effector 126. As shown in FIG. 8B, a pair of DC blocking capacitors $C_{bl1}$ 280-1 and $C_{bl2}$ 280-2 is provided to prevent any DC signal being applied to the load 259.

In one embodiment, the transformer 255 may be implemented with a Core Diameter (mm), Wire Diameter (mm), and Gap between secondary windings in accordance with the following specifications:

Core Diameter, D (mm)
D=19.9×10−3
Wire diameter, W (mm) for 22 AWG wire
W=7.366×10−4
Gap between secondary windings, in gap=0.125
G=gap/25.4

In this embodiment, the amount of electrical power supplied to the end effector 126 is controlled by varying the frequency of the switching signals used to switch the FET's 243. This works because the resonant circuit 250 acts as a frequency dependent (loss less) attenuator. The closer the drive signal is to the resonant frequency of the resonant circuit 250, the less the drive signal is attenuated. Similarly, as the frequency of the drive signal is moved away from the resonant frequency of the circuit 250, the more the drive signal is attenuated and so the power supplied to the load reduces. In this embodiment, the frequency of the switching signals generated by the FET gate drive circuitry 245 is controlled by a controller 281 based on a desired power to be delivered to the load 259 and measurements of the load voltage ($V_L$) and of the load current ($I_L$) obtained by conventional voltage sensing circuitry 283 and current sensing circuitry 285. The way that the controller 281 operates will be described in more detail below.

In one embodiment, the voltage sensing circuitry 283 and the current sensing circuitry 285 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 283 and the current sensing circuitry 285. In one-embodiment, a step-down regulator (e.g., LT1502 by Linear Technologies) may be employed by the power save circuit to reduce the supply voltage of the rail-to-rail amplifiers and thus extend the life of the battery 237.

Figure 8C:
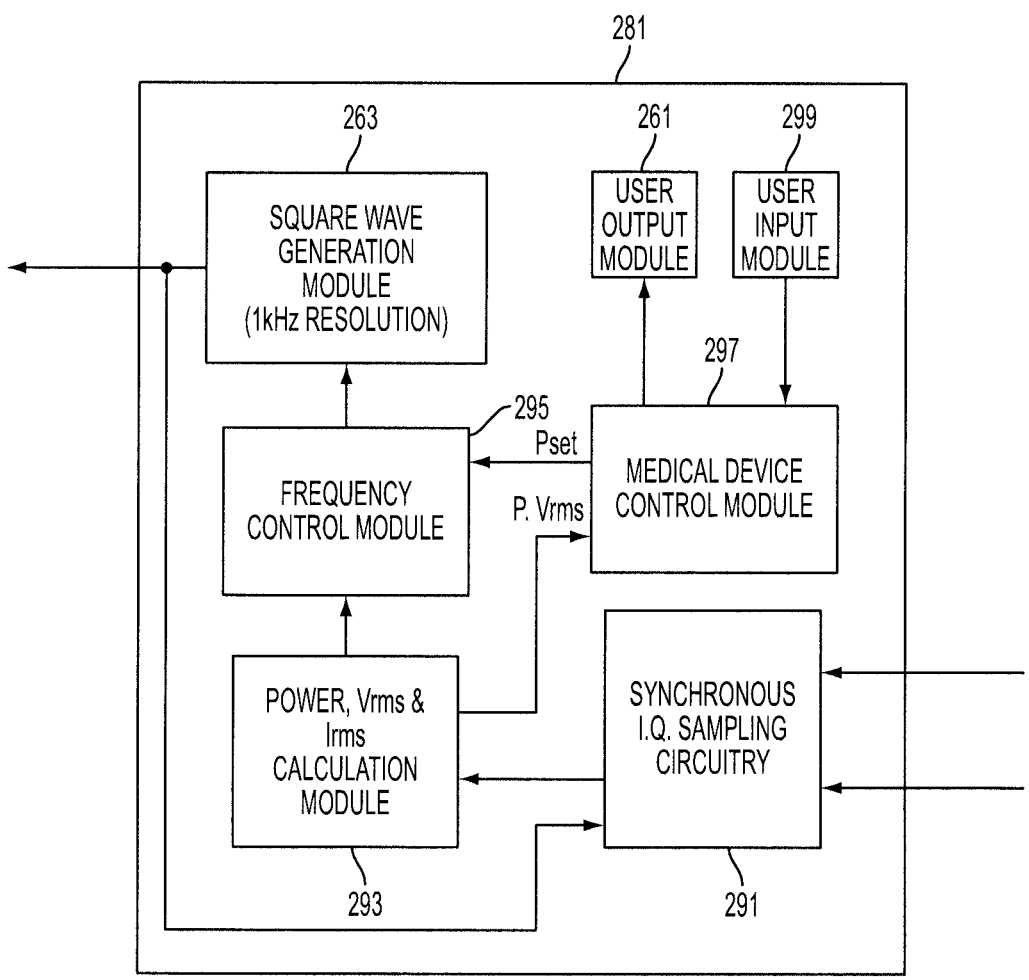
FIG. 8C shows one embodiment of the main components of a control circuit.

FIG. 8C shows the main components of the controller 281, according to one embodiment. In the embodiment illustrated in FIG. 8C, the controller 281 is a microprocessor based controller and so most of the components illustrated in FIG. 8c are software based components. Nevertheless, a hardware based controller 281 may be used instead. As shown, the controller 281 includes synchronous I,Q sampling circuitry 291 that receives the sensed voltage and current signals from the sensing circuitry 283 and 285 and obtains corresponding samples which are passed to a power, $V_{rms}$ and $I_{rms}$ calculation module 293. The calculation module 293 uses the received samples to calculate the RMS voltage and RMS current applied to the load 259 (FIG. 8B; end effector 126 and tissue/vessel gripped thereby) and from them the power that is presently being supplied to the load 259. The determined values are then passed to a frequency control module 295 and a medical device control module 297. The medical device control module 297 uses the values to determine the present impedance of the load 259 and based on this determined impedance and a pre-defined algorithm, determines what set point power ($P_{set}$) should be applied to the frequency control module 295. The medical device control module 297 is in turn controlled by signals received from a user input module 299 that receives inputs from the user (for example pressing buttons 228 or activating the control levers 221 on the handle 212) and also controls output devices (lights, a display, speaker or the like) on the handle 212 via a user output module 261.

The frequency control module 295 uses the values obtained from the calculation module 293 and the power set point ($P_{set}$) obtained from the medical device control module 297 and predefined system limits (to be explained below), to determine whether or not to increase or decrease the applied frequency. The result of this decision is then passed to a square wave generation module 263 which, in this embodiment, increments or decrements the frequency of a square wave signal that it generates by 1 kHz, depending on the received decision. As those skilled in the art will appreciate, in an alternative embodiment, the frequency control module 295 may determine not only whether to increase or decrease the frequency, but also the amount of frequency change required. In this case, the square wave generation module 263 would generate the corresponding square wave signal with the desired frequency shift. In this embodiment, the square wave signal generated by the square wave generation module 263 is output to the FET gate drive circuitry 245, which amplifies the signal and then applies it to the FET 243-1. The FET gate drive circuitry 245 also inverts the signal applied to the FET 243-1 and applies the inverted signal to the FET 243-2.

The electrosurgical instrument 210 may comprise additional features as discussed with respect to the electrosurgical system 100 illustrated in FIGS. 1-6. Those skilled in the art will recognize that electrosurgical instrument 210 may include a rotation knob 148, an elongated shaft 114, and an end effector 126. These elements function in a substantially similar manner to that discussed above with respect to the electrosurgical system 100 illustrated in FIGS. 1-6. In one example embodiment, the cordless electrosurgical instrument 210 may include visual indicators 235. The visual indicators 235 may provide a visual indication signal to an operator. In one example embodiment, the visual indication signal may alert an operator that the device is on, or that the device is applying energy to the end effector. Those skilled in the art will recognize that the visual indicators 235 may be configured to provide information on multiple states of the device.

According to various embodiments, the electrosurgical systems herein may be programmed to limit the rise of tissue impedance during the initial and middle parts of the coagulation cycle by limiting the power available in the higher impedances. As the natural tendency of tissue being treated in vessel sealing electrosurgical systems is to exhibit a dramatic rise in impedance at a certain point in the process, this may allow the impedance to rise more slowly than it would if a full range load curve were applied to the tissue. When tissue is grasped by an end effector with bipolar electrodes and a full range load curve is applied, there is sometimes a short time when the tissue impedance makes a drastic change from the lower impedance to the higher impedances. This is when the tissue and especially the fluids associated with that tissue are going through phase change. If the power is limited at the impedances that are expected to be encountered during this transition then the rate of rise in the impedance will be limited. This desired effect may have benefits in producing desired tissue effects and can reduce the power delivered to the tissue as the water begins to boil and reduce the popping that is occasionally seen in electrosurgical instruments.

The electrosurgical systems 100, 200 (e.g., the generators 120, 220) may be programmed to provide power to a tissue bite between jaws 164a, 164b according to any suitable method or algorithm. For example, in some embodiments, the generator 120, 220 may provide an electrosurgical drive signal according to one or more power curves. A power curve may define a relationship between power delivered to the tissue and the impedance of the tissue. For example as the impedance of the tissue changes (e.g., increases) during coagulation, the power provided by the generator 120, 220 may also change (e.g., decrease) according to the applied power curve.

Different power curves may be particularly suited, or ill-suited, to different types and/or sizes of tissue bites. Aggressive power curves (e.g., power curves calling for high power levels) may be suited for large tissue bites. When applied to smaller tissue bites, such as small vessels, more aggressive power curves may lead to exterior searing or other deleterious effects. Exterior searing may reduce the coagulation/weld quality at the exterior and can also prevent complete coagulation of interior portions of the tissue. Similarly, less aggressive power curves may fail to achieve hemostasis when applied to larger tissue bites (e.g., larger bundles).

Figure 9:
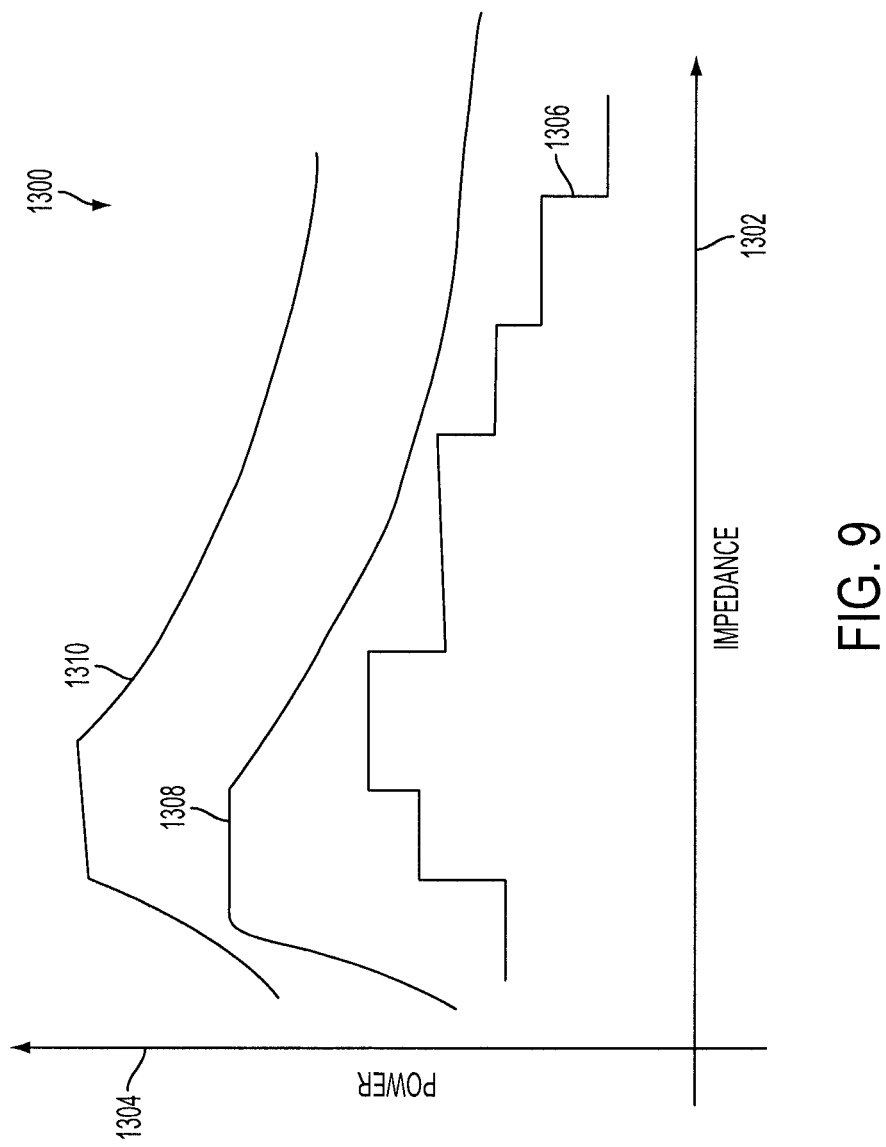
FIG. 9 shows one embodiment of a chart showing example power curves that may be delivered by an electrosurgical system.

FIG. 9 shows one embodiment of a chart 1300 showing example power curves 1306, 1308, 1310. The chart 1300 comprises an impedance axis 1302 showing increasing potential tissue impedances from left to right. A power axis 1304 shows increasing power from down to up. Each of the power curves 1306, 1308, 1310 may define a set of power levels, on the power axis 1304, corresponding to a plurality of potential sensed tissue impedances, in the impedance axis 1302. In general, power curves may take different shapes, and this is illustrated in FIG. 9. Power curve 1306 is shown with a step-wise shape, while power curves 1308, 1310 are shown with curved shapes. It will be appreciated that power curves utilized by various embodiments may take any usable continuous or non-continuous shape. The rate of power delivery or aggressiveness of a power curve may be indicated by its position on the chart 1300. For example, power curves that deliver higher power for a given tissue impedance may be considered more aggressive. Accordingly, between two power curves, the curve positioned highest on the power axis 1304 may be the more aggressive. It will be appreciated that some power curves may overlap.

The aggressiveness of two power curves may be compared according to any suitable method. For example, a first power curve may be considered more aggressive than a second power curve over a given range of potential tissue impedances if the first power curve has a higher delivered power corresponding to at least half of the range of potential tissue impedances. Also, for example, a first power curve may be considered more aggressive than a second power curve over a given range of potential tissue impedances if the area under the first curve over the range is larger than the area under the second curve over the range. Equivalently, when power curves are expressed discretely, a first power curve may be considered more aggressive than a second power curve over a given set of potential tissue impedances if the sum of the power values for the first power curve over the set of potential tissue impedances is greater than the sum of the power values for the second power curve over the set of potential tissue impedances.

As described herein, some embodiments of the instrument 110 comprise a positive temperature coefficient (PTC) material positioned between one or both of the electrodes of the jaw members 164a, 164b. The PTC material may have an impedance profile that remains relatively low and relatively constant until it reaches a threshold or trigger temperature, at which point the impedance of the PTC material may increase. In use, the PTC material may be placed in contact with the tissue while power is applied. The trigger temperature of the PTC material may be selected such that it corresponds to a tissue temperature indicating the completion of welding or coagulation. Accordingly, as a welding or coagulation process is completed, the temperature of the PTC material may increase, causing a corresponding increase in the impedance of the PTC material. This additional series impedance, in series with the tissue, may cause a decrease in power actually provided to the tissue.

It will be appreciated that during the coagulation or welding process, tissue impedance may generally increase. In some embodiments, tissue impedance may display a sudden impedance increase indicating successful coagulation. The increase may be due to physiological changes in the tissue, a PTC material reaching its trigger threshold, etc. The amount of energy that may be required to bring about the sudden impedance increase may be related to the thermal mass of the tissue being acted upon. The thermal mass of any given tissue bite, in turn, may be related to the type and amount of tissue in the bite.

Various embodiments may utilize this sudden increase in tissue impedance to select an appropriate power curve for a given tissue bite. For example, the generator 120, 220 may select and apply successively more aggressive power curves until the tissue impedance reaches an impedance threshold indicating that the sudden increase has occurred. For example, reaching the impedance threshold may indicate that coagulation is progressing appropriately with the currently applied power curve. The impedance threshold may be a tissue impedance value, a rate of change of tissue impedance, and/or a combination of impedance and rate of change. For example, the impedance threshold may be met when a certain impedance value and/or rate of change are observed. According to various embodiments, different power curves may have different impedance thresholds, as described herein.

Figure 10:
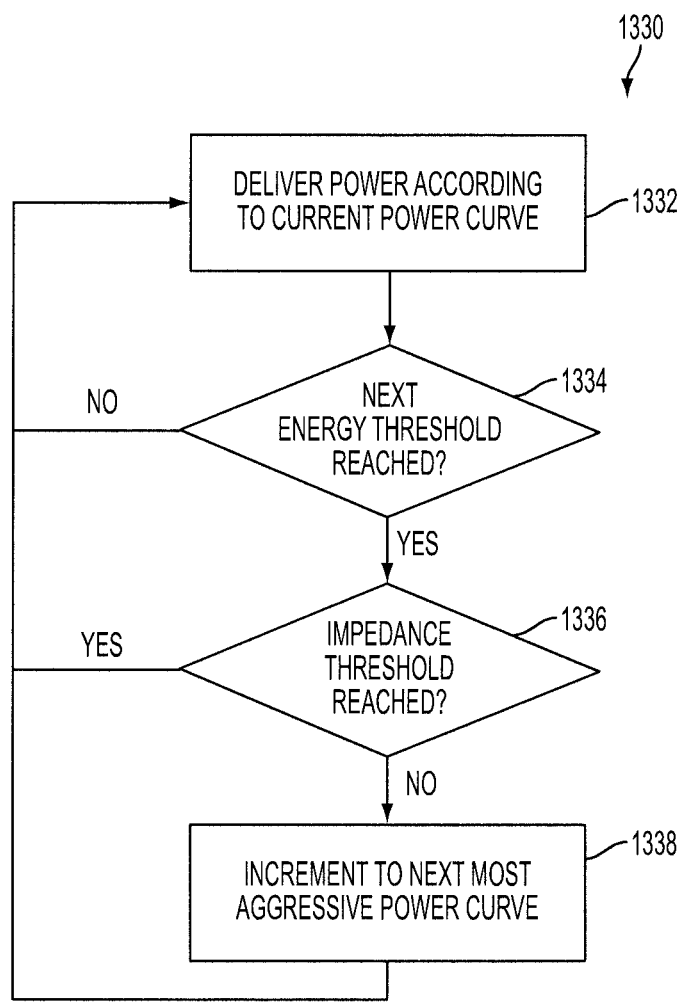
FIG. 10 shows one embodiment of a process flow for applying one or more power curves to a tissue bite.

FIG. 10 shows one embodiment of a process flow 1330 for applying one or more power curves to a tissue bite. Any suitable number of power curves may be used. The power curves may be successively applied in order of aggressiveness until one of the power curves drives the tissue to the impedance threshold. At 1332, the generator 120, 220 may apply a first power curve. According to various embodiments, the first power curve may be selected to deliver power at a relatively low rate. For example, the first power curve may be selected to avoid tissue searing with the smallest and most vulnerable expected tissue bites.

The first power curve may be applied to the tissue in any suitable manner. For example, the generator 120, 220 may generate a drive signal implementing the first power curve. The power curve may be implemented by modulating the power of the drive signal. The power of the drive signal may be modulated in any suitable manner. For example, the voltage and/or current of the signal may be modulated. Also, in various embodiments, the drive signal may be pulsed. For example, the generator 120, 220 may modulate the average power by changing the frequency, pulse width, duty cycle, etc. of the drive signal. The drive signal may be provided to the electrodes of the first and second jaw members 164a, 164b.

While applying the first power curve, the generator 120, 220 may monitor the total energy provided to the tissue. The impedance of the tissue may be compared to the impedance threshold at one or more energy thresholds. There may be any suitable number of energy thresholds, which may be selected according to any suitable methodology. For example, the energy thresholds may be selected to correspond to known points where different tissue types achieve the impedance threshold. At 1334, the generator 120, 220 may determine whether the total energy delivered to the tissue has met or exceeded a first energy threshold. If the total energy has not yet reached the first energy threshold, the generator 120, 220 may continue to apply the first power curve at 1332.

If the total energy has reached the first energy threshold, the generator 120, 220 may determine whether the impedance threshold has been reached (1336). As described above, the impedance threshold may be a predetermined rate of impedance change (e.g., increase) a predetermined impedance, or combination of the two. If the impedance threshold is reached, the generator 120, 220 may continue to apply the first power curve at 1332. For example, reaching the impedance threshold in the first power curve may indicate that the aggressiveness of the first power curve is sufficient to bring about suitable coagulation or welding.

In the event that the impedance threshold is not reached at 1336, the generator 120, 220 may increment to the next most aggressive power curve at 1338 and apply the power curve as the current power curve at 1332. In some embodiments, incrementing to the next most aggressive power curve may comprise applying a multiplier to a less aggressive power curve such as, for example, the previously implemented power curve. When the next energy threshold is reached at 1334, the generator 120, 220 again may determine whether the impedance threshold is reached at 1336. If it is not reached, the generator 120, 220 may again increment to the next most aggressive power curve at 1338 and deliver that power curve at 1332.

The process flow 1330 may continue until terminated. For example, the process flow 1330 may be terminated when the impedance threshold is reached at 1336. Upon reaching the impedance threshold, the generator 120, 220 may apply the then-current power curve until coagulation or welding is complete. Also, for example, the process flow 1330 may terminate upon the exhaustion of all available power curves. Any suitable number of power curves may be used. If the most aggressive power curve fails to drive the tissue to the impedance threshold, the generator 120, 220 may continue to apply the most aggressive power curve until the process is otherwise terminated (e.g., by a clinician or upon reaching a final energy threshold).

According to various embodiments, the process flow 1330 may continue until the occurrence of a termination threshold. The termination threshold may indicate that coagulation and/or welding is complete. For example, the termination threshold may be based on one or more of tissue impedance, tissue temperature, tissue capacitance, tissue inductance, elapsed time, etc. Upon termination, the surgical system 100, 200 may generate an audible tone indicating termination. These may be a single termination threshold or, in various embodiments, different power curves may have different termination thresholds. According to various embodiments, different power curves may utilize different impedance thresholds. For example, the process flow 1330 may transition from a first to a second power curve if the first power curve has failed to drive the tissue to a first tissue impedance threshold and may, subsequently, shift from the second to a third power curve if the second power curve has failed to drive the tissue to a second impedance threshold. In some embodiments, rather than proceeding between power curves in order, the generator 120, 220 may skip one or more power curves. For example, if the impedance of the tissue at the end of a power curve exceeds a skip threshold, then generator 120, 220, instead of proceeding to the next power curve, may skip to a more aggressive power curve (e.g., a power curve that provides more energy for a given tissue impedance).

In some embodiments utilizing a pulsed drive signal, the generator 120, 220 may apply one or more composite load curves to the drive signal, and ultimately to the tissue. Composite load curves, like other power curves described herein, may define a level of power to be delivered to the tissue as a function of a measured tissue property or properties. Composite load curves may, additionally, define pulse characteristics, such as pulse width, in terms of the measured tissue properties (e.g., impedance, applied current, applied voltage, temperature, reflectivity, force applied to the tissue, etc.).

Figure 11:
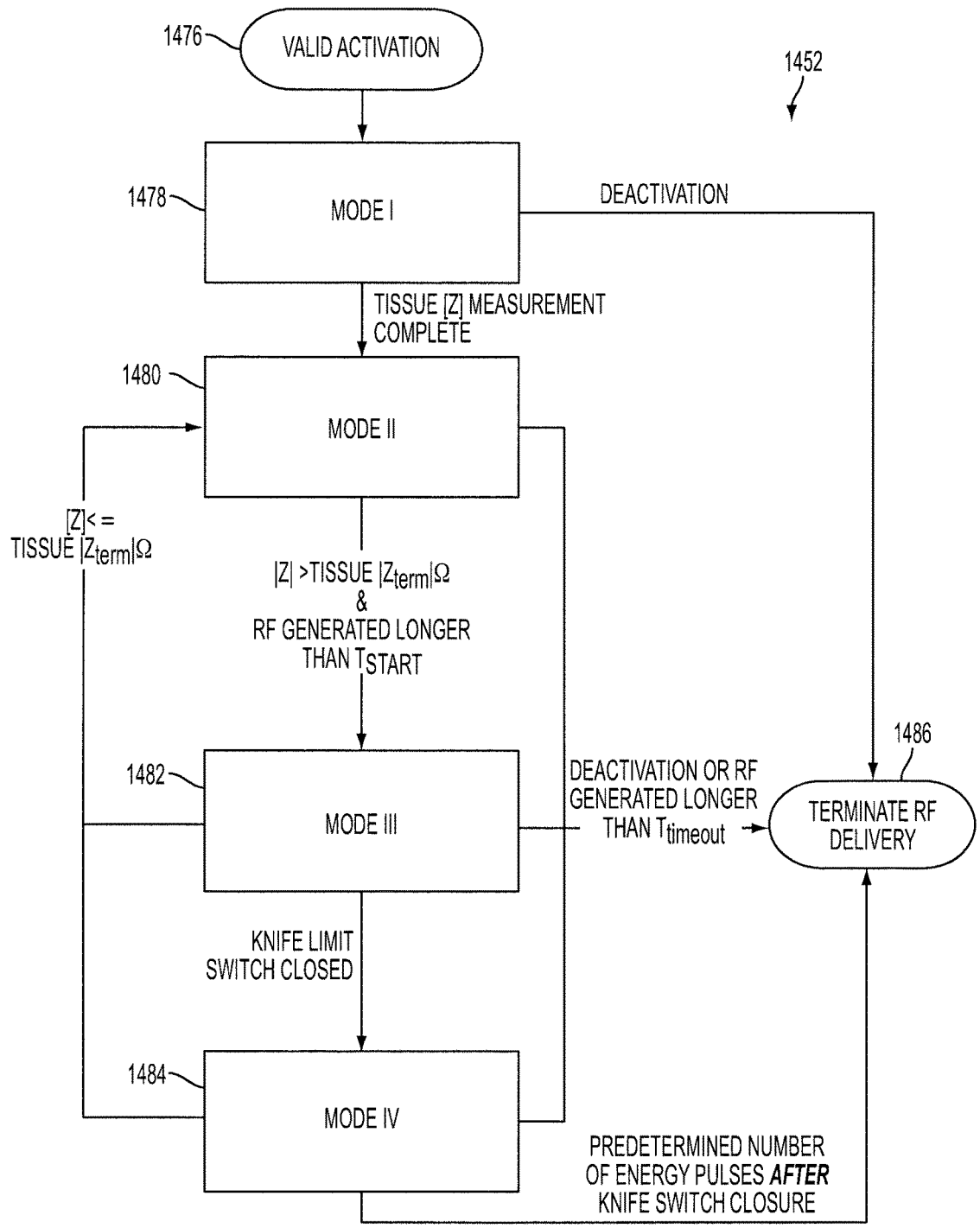
FIG. 11 shows one embodiment of a process flow for applying one or more power curves to a tissue bite.

FIG. 11 shows one embodiment of a process flow or algorithm 1452, as implemented by the generator 120, 220. The algorithm 1452 may be activated at 1476. It will be appreciated that the algorithm 1452 may be activated in any suitable manner. For example, the algorithm 1452 may be activated by a clinician upon actuation of the surgical device 104, 106 (e.g., by pulling or otherwise actuating the jaw closure trigger 121, button 128, etc.).

According to various embodiments, the algorithm 1452 may comprise a plurality of modes 1478, 1480, 1482, 1484. Each mode may represent a different stage of the cutting and coagulation of a tissue bite. For example, in the first mode 1478, the generator 120, 220 may perform an analysis of initial tissue conditions (e.g., impedance, etc.). In the second mode 1480, the generator 120, 220 may apply energy to the tissue in order to prepare the tissue for cutting. In the third or cut mode 1482, the generator 120, 220 may continue to apply energy while the instrument 110 cuts the tissue, for example, by advancing the cutting element 171. In the fourth or completion mode 1484, the generator 120, 220 may apply energy post-cut to complete coagulation.

Referring now to the first mode 1478, the generator 120, 220 may measure any suitable tissue condition or conditions including, for example, current, voltage, temperature, reflectivity, force applied to the tissue, etc. In various embodiments, an initial impedance of the tissue may be measured according to any suitable manner. For example, the generator 120, 220 may modulate the drive signal to provide a known voltage or currency to the tissue. Impedance may be derived from the known voltage and the measured current or vice versa. It will be appreciated that tissue impedance may alternately or additionally be measured in any other suitable manner. According to the algorithm 1452, the generator 120, 220 may proceed from the first mode 1478 to the second mode 1480. In various embodiments, the clinician may end the algorithm 1452 in the first mode 1478, for example, by deactivating the generator 120, 220 and/or the surgical device 110. If the clinician terminates the algorithm 1542, RF delivery may also be terminated at 1486.

In the second mode 1480, the generator 120, 220 may begin to apply energy to the tissue via the drive signal to prepare the tissue for cutting. In embodiments utilizing a pulsed drive signal, applying energy according to the second mode 1480 may comprise modulating pulses onto the drive signal according to load curves including, for example, composite load curves. In various embodiments, load curves may be successively applied in the second mode in order of aggressiveness (e.g., to accommodate various types of tissue-volume clamped in the instrument jaws). The second mode 1480 may be terminated upon the occurrence of various events. For example, if the total RF application time has exceeded a timeout time, then the generator 120, 220 may end the tissue operation by terminating RF delivery at 1486. Also, various events may cause the generator 120, 220 to transition from the second mode 1480 to the third mode 1482. For example, the generator 120, 220 may transition to the third mode 1482 when the tissue impedance (Z) exceeds a threshold tissue impedance ($Z_{term}$) and RF energy has been delivered for at least more than a minimum time ($T_{start}$). The threshold tissue impedance may be a fixed impedance or may be a function of other specific parameters or variables sensed by the instrument or generator. Examples of other parameters that may determine the threshold tissue impedance include minimum impedance, compressive forces on tissue, etc. Additionally, the threshold impedance may be set as a function of the rate of change of the tissue impedance by observing the rate of change of the tissue impedance and calculating a corresponding impedance threshold value.

According to various embodiments, if the final load curve 1462 is completed in the second mode 1480 before completion of the second mode 1480, then the final power curve 1462 may be continuously applied, for example, until the tissue impedance threshold is met, the maximum second mode time is reached and/or the timeout time is reached. Also, it will be appreciated that, with some tissue cuts, the second mode 1480 may be completed before all available consolidated load curves 1456, 1458, 1460, 1462 are executed.

At the third mode 1482, the generator 120, 220 may continue to modulate pulses onto the drive signal. Generally, third mode pulses may be modulated onto the drive signal according to any suitable manner including, for example, that described above with reference to the process flow 1488. The power and pulse characteristics of the third mode pulses may be determined according to any suitable method and, in various embodiments, may be determined based on the composite load curve that was being executed at the completion of the second mode 1480 (the current load curve). According to various embodiments, the current load curve may be utilized to determine the pulse power of third mode pulses, while the pulse characteristics (e.g., pulse width, ramp time, fall time, off time, etc.) may be constant regardless of composite load curve. In some embodiments, the third mode 1482 may utilize a third-mode-specific composite load curve that may be one of the load curves 1456, 1458, 1460, 1462 utilized in the second mode 1480, or may be a different composite load curve (not shown).

The generator 120, 220 may continue to execute the third mode 1482 until receiving an indication that the tissue cut is complete. In embodiments utilizing surgical implements having a knife or other cutting element, such as 171, the indication may be received when the cutting element 171 reaches its distal-most position. This may trip a knife limit sensor (not shown) indicating that the cutting element 171 has reached the end of its throw. Upon receiving the indication that the tissue cut is complete, the generator 120, 220 may continue to the fourth mode 1484. It will also be appreciated that, in some embodiments, the generator 120, 220 may transition from the third mode 1482 directly to RF termination at 1486, for example, if the timeout time has been reached.

In the fourth mode 1484, the generator 120, 220 may provide an energy profile designed to complete coagulation of the now-cut tissue. For example, according to various embodiments, the generator 120, 220 may provide a predetermined number of pulses. The pulses may be provided in a manner similar to that described above with respect to the process flow 1488. The power and pulse characteristics of the pulses may be determined according to any suitable manner. For example, power and pulse characteristics of the fourth mode pulses may be determined based on the current composite load curve, the third-mode-specific load curve, or a fourth-mode-specific composite load curve. In some embodiments, power may be determined based on the current composite load curve, while pulse characteristics may be fourth mode-specific. Also, according to various embodiments, the power and pulse characteristics of fourth mode pulses may be determined independent of the current composite load curve. In some embodiments, the electrosurgical system 100, 200 may be configured to generate an audible tone upon termination of RF delivery at 1486.

According to various embodiments, it is desirable to manage the rise of tissue impedance during treatment of a tissue bite (a treatment cycle, or cycle). During coagulation, tissue impedance serves as an abstraction of the condition of the tissue. Changes in tissue impedance correlate to changes in the tissue itself that are indicators of the degree of completion of the coagulation. Accordingly, many drive signal algorithms look for a threshold tissue impedance to determine when during a treatment cycle coagulation is complete. The tissue impedance during a treatment cycle also provides indications of the properties of the resulting coagulation or seal. For example, the quality of coagulation can be increased by managing the rate of impedance increase during a treatment cycle.

According to various embodiments, the electrosurgical system 100, 200 (e.g., the generator 120, 220 thereof) is programmed to manage the rate of impedance increase during tissue treatment. In some embodiments, the generator 120, 220 is programmed to implement multiple successive drive signal modes or modes. Within each mode, the generator 120, 220 may modulate the drive signal to reduce the amount of power provided to the tissue when the tissue impedance exceeds one or more threshold values. For example, if the tissue impedance during application of a mode exceeds a threshold impedance value for that mode, the generator 120, 220 may reduce the power made available to tissue via the drive signal. This may be implemented by direct limits on the power of the drive signal or indirectly by limiting the voltage level of the drive signal. In various embodiments some or all of the modes may have multiple impedance thresholds. For example, the generator 120, 220 may reduce the power of the drive signal further as successively higher impedance thresholds are reached. The threshold impedances, as well as the power provided after the threshold impedances, may generally increase as the system 100, 200 progresses from mode to mode.

The duration of each mode may be determined in any suitable manner. For example, in some embodiments, some or all of the modes may be applied for a predetermined amount of time or application period. Also, in various embodiments, some or all of the modes may be applied for a predetermined amount of time after a threshold tissue impedance for the mode is met. It will be appreciated that specific values, including the number of modes, the tissue impedance threshold or thresholds for each mode, application period of each mode, etc., may vary from application to application. For example, these values may vary based on the size and shape of the electrodes being used, the type of tissue being treated, etc.

Figure 12:
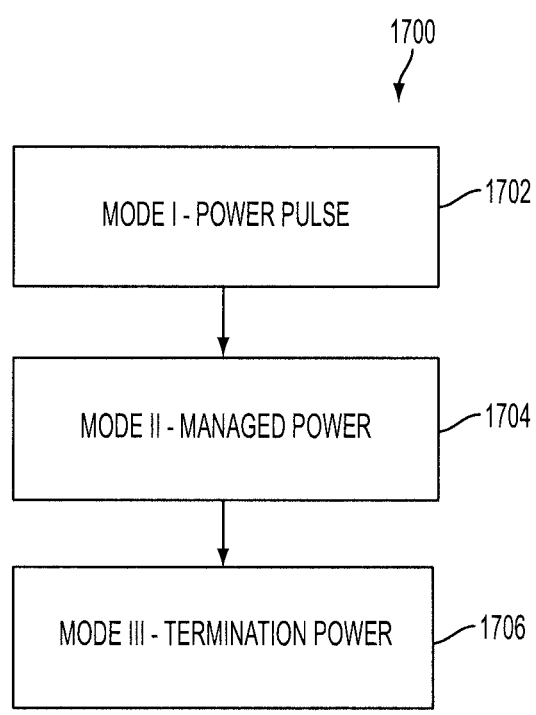
FIG. 12 shows one embodiment of a process flow for managing tissue impedance during a treatment cycle utilizing three modes.
Figure 12A:
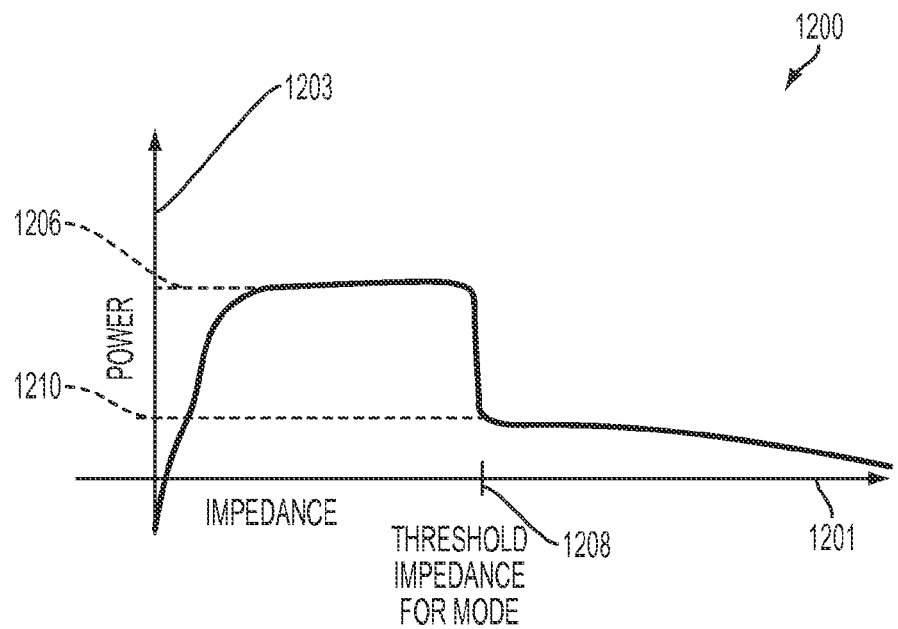
FIG. 12a is a chart showing power and impedance characteristics of one embodiment of a drive signal that may be provided by the generator during the first mode of the process flow of FIG. 12.

According to various embodiments, three modes may be utilized. FIG. 12 shows one embodiment of a process flow 1700 for managing tissue impedance during a treatment cycle utilizing three modes. The treatment cycle is initiated with a first mode 1702. FIG. 12a is a chart showing power and impedance characteristics of one embodiment of a drive signal that may be provided by the generator 120, 220 during the first mode 1702. In FIG. 12, impedance is indicated in axis 1201 and power is indicated on axis 1203. During the first mode 1702, the generator 120, 220 may be configured to provide a first power threshold 1206 to the tissue while the tissue impedance is below a threshold impedance 1208 for the mode 1702. If the impedance of the tissue exceeds the threshold impedance 1208 for the mode 1702, the generator 120, 220 may limit the provided power to a second power threshold 1210. In various embodiments, the second power threshold 1210 may be less than the maximum power that the generator 120, 220 is configured to deliver to the tissue. In this way, the first mode 1702 may prepare the tissue for greater power application in later modes. The application period for the first mode 1702 may be any suitable value including, for example, one second. It will be appreciated that the drive signal may be pulsed during application of the first mode 1702. For example, the mode 1702 may be applied as a single pulse lasting the duration of the application time period for the mode 1702, or in multiple shorter pulses. In embodiments utilizing multiple pulses in the mode 1702, each pulse may conform to impedance-determined limits for drive signal power, as described.

Figure 12B:
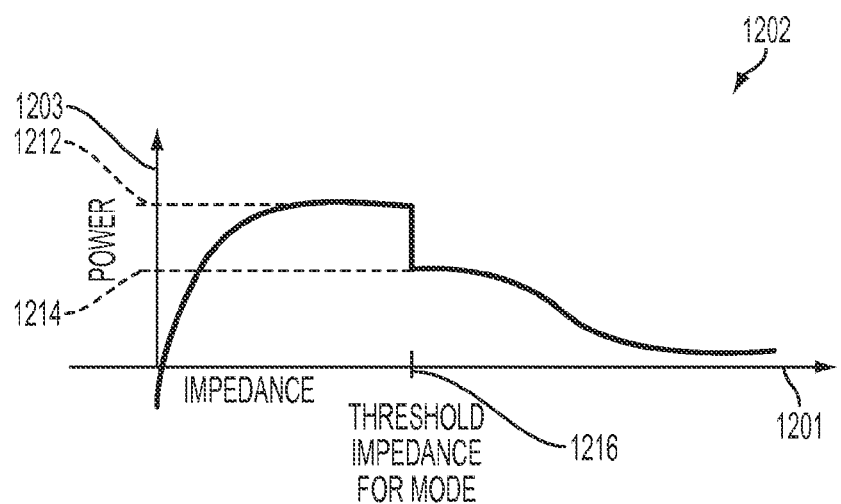
FIG. 12b is a chart showing power and impedance characteristics of one embodiment of a drive signal that may be provided by the generator during the second mode of the process flow of FIG. 12.

FIG. 12b is a chart showing power and impedance characteristics of one embodiment of a drive signal that may be provided by the generator 120, 220 during the second mode 1704. In the second mode 1704, the generator 120, 220 provides a relatively high level of power at the lowest tissue impedances expected to be encountered. For example, in some embodiments, the full power available from the generator (1212 in FIG. 12b) may be provided at tissue impedances below the threshold impedance 1216 for the second mode 1704. Above the threshold impedance 1216, the power may be reduced below a second power threshold 1214 so as to limit the rate of impedance increase. In some embodiments, the second power threshold 1214 is greater than the second power threshold 1210 of the first mode 1702. Also, it will be appreciated that the impedance threshold 1208 of the first mode 1702 and the impedance threshold 1216 of the second mode 1704 may be equal or may take different values depending on the implementation. The application period of the second mode may be longer than that of the first mode so as to allow the provided energy to act on the tissue. For example, in some embodiments, the application period of the second period is between four and five seconds. It will be appreciated that the drive signal may also be provided as a single pulse lasting the duration of the application period and/or as multiple pulses. Again, when multiple pulses are used, each pulse may conform to the impedance-determined limits for drive signal power.

Figure 12C:
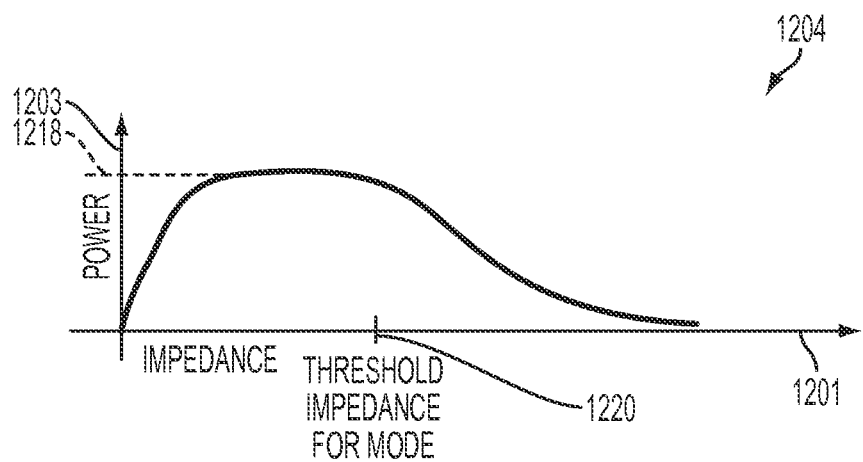
FIG. 12c is a chart showing power and impedance characteristics of one embodiment of a drive signal that may be provided by the generator during the third mode of the process flow of FIG. 12.

FIG. 12c is a chart showing power and impedance characteristics of one embodiment of a drive signal that may be provided by the generator 120, 220 during the third mode 1706. In the third mode 1706, the generator 120, 220 provides a drive signal with a drive signal power limit 1218 configured to drive the tissue impedance to a final value indicating completion of the tissue cycle. For example, if tissue impedance remains below a threshold value 1220 for the mode 1706, the generator 120, 220 may provide a relatively high level of power 1218. In some embodiments, the drive signal power limit 1218 may be the maximum power available from the generator 120, 220. Above the threshold impedance, the generator 120, 220 may provide a lower level of power. The above-threshold power provided in the third mode 1706, for example, may be higher than the above-threshold power provided in the second mode 1704. This may allow the tissue impedance to rise faster in the third mode 1706 towards a final target impedance. In some embodiments, the above-threshold power provided in the third mode 1706 may be up to the limit 1218. In some embodiments, the third mode 1706 may comprise multiple sub-modes that successively raise the above-threshold power so as to drive the tissue to the final target impedance indicating completion of the tissue cycle. Each sub-mode may be applied as one or more pulses. The application period of the sub-modes may be determined in any suitable manner. For example, the application period of the third mode may be divided into multiple sub-periods, with each sub-period corresponding to a sub-mode. Also, in some embodiments, each sub-mode may comprise a pulse of a predetermined time that is applied as part of the drive signal.

In some embodiments, the third mode (e.g., the final sub-mode thereof) may be applied until the tissue impedance increases to a level indicating completion of coagulation or the end of the tissue cycle (e.g., a final termination impedance). In some embodiments, the final termination impedance may be 300Ω.

Figure 13:
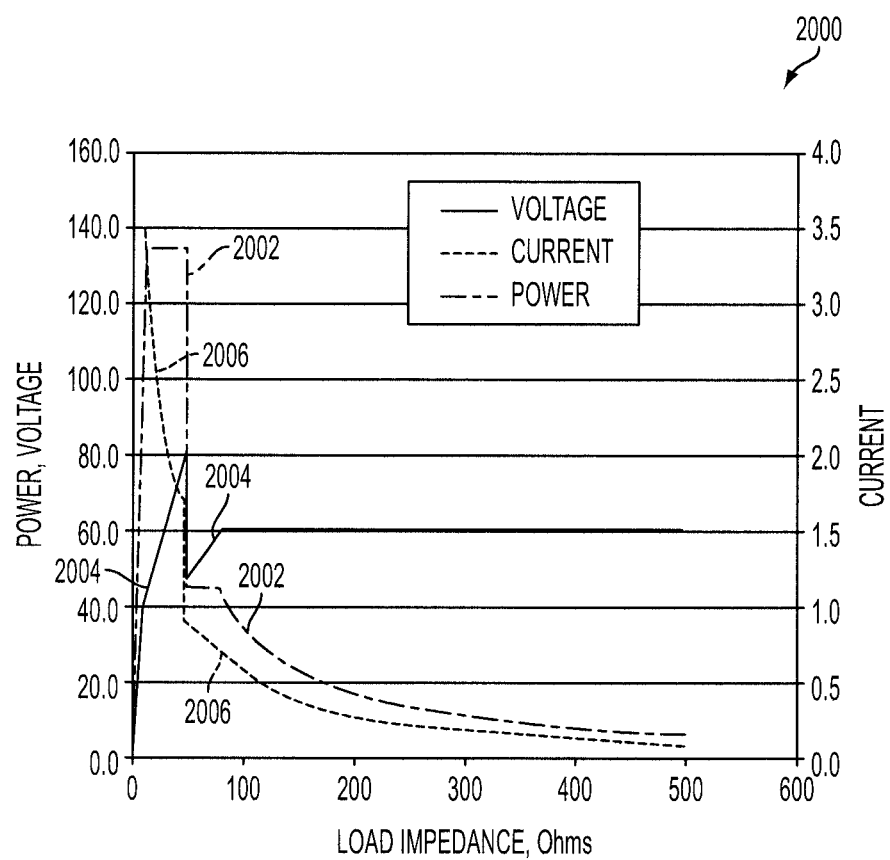
FIG. 13 is a chart showing voltage and tissue impedance thresholds that may be applied during the first mode according to one embodiment.

FIG. 13 is a chart 2000 showing voltage and tissue impedance thresholds that may be applied during a first mode, such as the first mode 1702, according to one embodiment. In the chart 2000, load or tissue impedance is expressed on the horizontal axis while current 2006, voltage 2004 and power 2002 are expressed on the vertical axis. Values for current 2006, voltage 2004 and power 2002 shown in FIG. 13 represent the maximum values for these quantities permitted during the first mode 1702 as a function of tissue impedance. In the example shown in FIG. 13, two impedance thresholds are utilized. When the tissue impedance is below a first threshold (e.g., 75Ω), a maximum voltage of the drive signal is limited to 80 Volts. This, practically, limits the power to 135 Watts, as illustrated. Between the first threshold and a second threshold (e.g., 100Ω), the maximum voltage of the drive signal ramps between 50 Volts and 60 Volts, which limits the drive signal power to 45 Watts. Above the second threshold, drive signal voltage is limited to 60 Volts. As illustrated, this limits the power 2002 of the drive signal to 45 Watts or less, with power decreasing as tissue impedance increases. The application period of the first mode as described in FIG. 13 may be, for example one second. Because the values shown in FIG. 13 are thresholds, it will be appreciated that not every application of the first mode in the manner shown in FIG. 13 will result in the full range of tissue impedances shown. Also, as described above, the first mode of FIG. 13 may be implemented as a single pulse or as multiple pulses during the application period.

Figure 14:
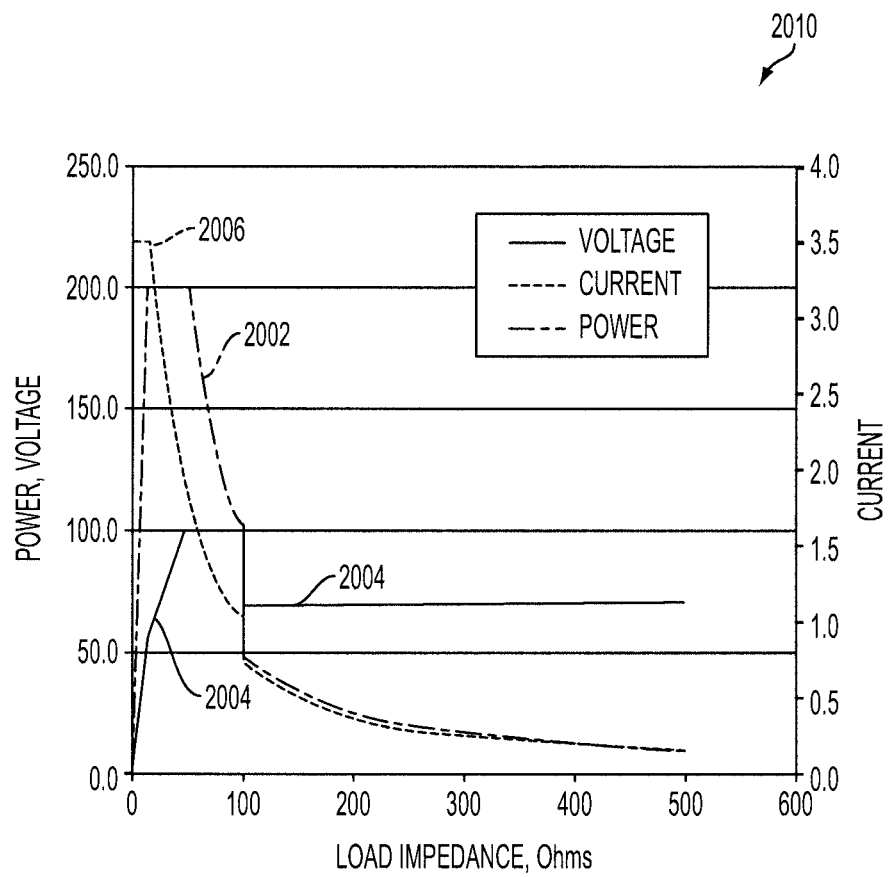
FIG. 14 is a chart showing voltage and tissue impedance thresholds that may be applied during a second mode according to one embodiment.

FIG. 14 is a chart 2010 showing voltage and tissue impedance thresholds that may be applied during a second mode, such as the second mode 1704, according to one embodiment. The example of FIG. 14, like the example of FIG. 13, shows two impedance thresholds within the second mode. When tissue impedance is less than the first threshold (e.g., 50Ω), the drive signal voltage may be limited to 100 Volts, resulting in a drive signal power of 200 Watts or less. In some embodiments, this may represent the maximum power that the generator 120, 220 is configured to deliver to tissue. Between the first impedance threshold and the second impedance threshold (e.g., 100Ω in FIG. 14), the drive signal voltage may be limited to a second level (e.g., 100 Volts in FIG. 14). This may cause the drive signal power 2002 to be reduced, as shown. At above the second impedance threshold, the generator 120, 220 may limit the voltage of the drive signal to a second threshold level (e.g., 75 Volts). This may further limit the power 2002 to less than 50 Watts, as illustrated. In some embodiments, the application period of the second mode illustrated in FIG. 14 is between four and five seconds. Again, because the values shown in FIG. 14 are thresholds, it will be appreciated that not every application of the second mode, as illustrated, will result in the full range of tissue impedances shown. Also, it will be appreciated that the drive signal may be pulsed during application of the second mode. For example, the second mode may be applied as a single pulse lasting the duration of the application time period, or in multiple shorter pulses. In embodiments utilizing multiple pulses, each pulse may conform to the thresholds for drive signal power 2002 and voltage 2004, for example, as illustrated in FIG. 14.

Figure 15:
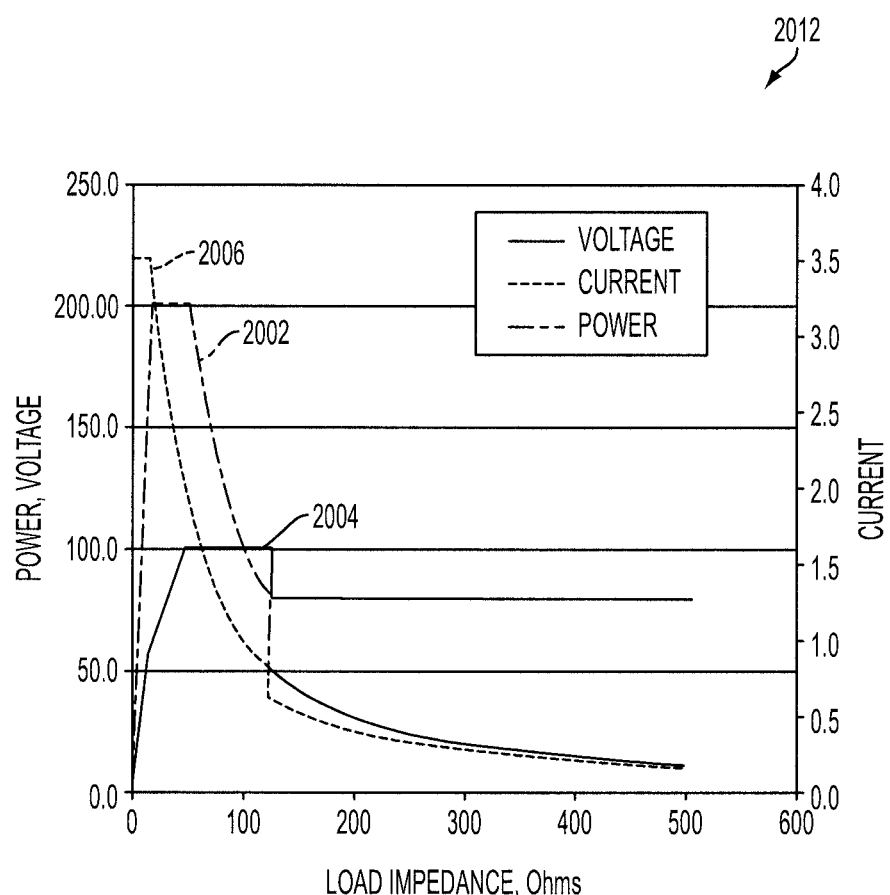
FIG. 15 is a chart showing voltage and impedance thresholds for a first sub-mode of the third mode.

As described herein, the third mode, or termination mode, may comprise a plurality of sub-modes comprising different impedance thresholds and corresponding power or voltage limits. FIG. 15 is a chart 2012 showing voltage and impedance thresholds for a first sub-mode of the third mode, such as the third mode 1706. It will be appreciated that the first sub-mode may be applied as a single pulse or as multiple pulses. The example first sub-mode shown in FIG. 15 utilizes a single impedance threshold at 120Ω. When the tissue impedance is below 120Ω, the generator 120, 220 may provide a relatively high level of power. In FIG. 15, this is indicated by a voltage limit of 100V, corresponding to a drive signal power limit of 200 Watts, which may represent the maximum power of the generator 120, 220. In some embodiments, if the tissue is still below the threshold value of the first sub-mode, it may require high power to complete coagulation by the end of the termination mode. Beyond the impedance threshold, the voltage of the drive signal is limited to 70 Volts, resulting in a drive signal power 2002 of less than 50 Watts, as shown. The first sub-mode of FIG. 15 may be applied as one or more pulses and may have an application period, for example of one second.

Figure 16:
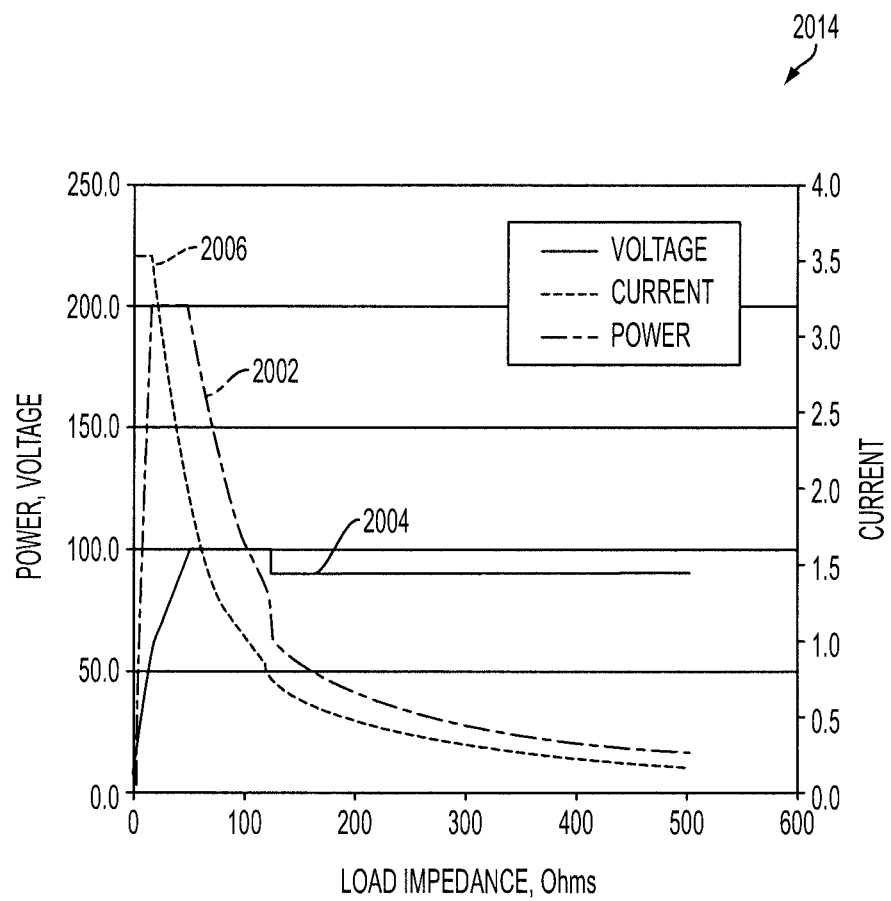
FIG. 16 is a chart showing voltage and impedance thresholds for a second sub-mode of a third mode.
Figure 17:
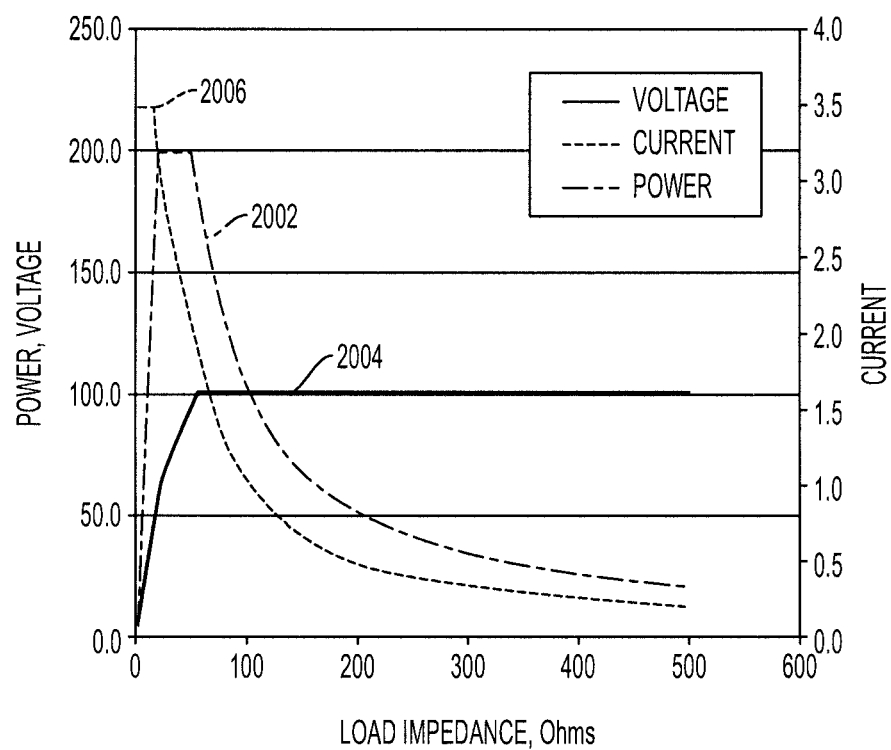
FIG. 17 is a chart showing voltage and impedance thresholds for a third sub-mode of a third mode.

Subsequent sub-modes of the third or termination mode may increase the power of the post-threshold drive signal. For example, FIG. 16 is a chart 2014 showing voltage and impedance thresholds for a second sub-mode of a third mode, such as the third mode 1706. In FIG. 16, the post-threshold drive signal voltage 2004 is limited to 85 Volts, allowing a higher post-threshold drive signal power 2002. The second sub-mode of FIG. 16 may be applied as one or more pulses and may have an application period of one second. Finally, FIG. 17 is a chart 2016 showing voltage and impedance thresholds for a third sub-mode of a third mode, such as the third mode 1706. In the third sub-mode, the drive signal voltage 2004 is limited to 100 Volts throughout the mode, allowing increased drive signal power 2002 relative to the first and second sub-modes illustrated in FIGS. 15 and 16. In some embodiments, the third sub-mode may entail the generator 120, 220 providing its maximum available power. The third sub-mode may be applied for a suitable application period and/or may be applied until the tissue reaches a final termination impedance indicating completion of coagulation and, therefore, completion of the tissue cycle.

Figure 18:
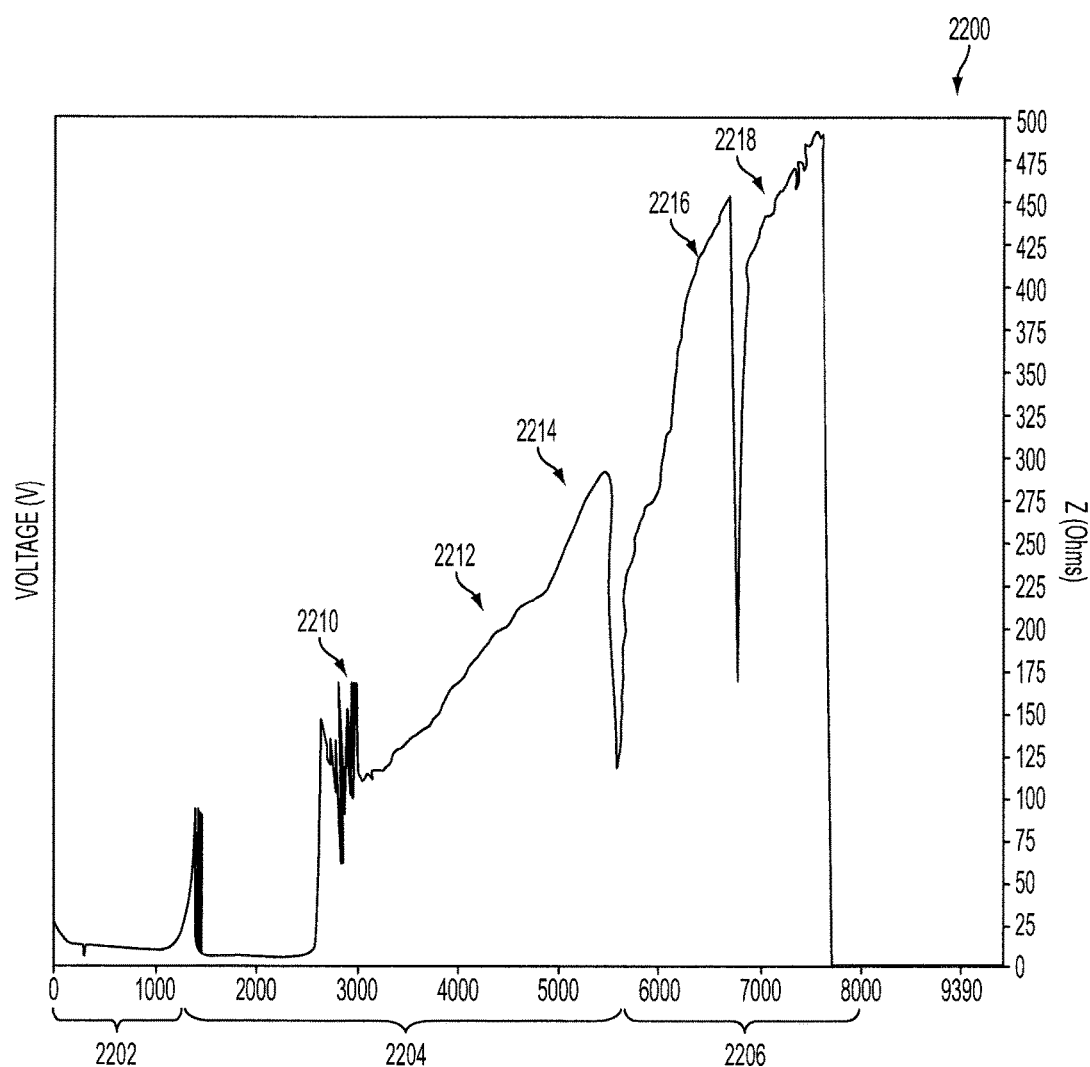
FIG. 18 is a chart showing tissue impedance during one tissue cycle according to the process flow of FIG. 12.

FIG. 18 is a chart 2200 showing tissue impedance during one tissue cycle according to the process flow 1700 and utilizing the threshold values illustrated in FIGS. 13-17. In the chart 2200, a first mode 2202, corresponding to FIG. 13, extends for an application period of 1.4 seconds, or 1,400 milliseconds. As illustrated, tissue impedance remains low (e.g., below 25Ω) for much of the first mode 2202 and begins to ramp up at the end. Instead of allowing the impedance to continue its high rate of increase, the generator 120, 220 begins a second mode 2204 at about 1.4 seconds and continues it for an application period of about four seconds to 5.4 seconds, or 5,400 milliseconds. As illustrated, the tissue impedance exceeds the first and second threshold impedances of the second mode 2204 at 2210, causing the generator 120, 220 to apply a constant voltage drive signal in at 2212. The result is a gently sloping increase in tissue impedance, as illustrated by 2212. Upon the expiration of the second mode 2204, the generator 120, 220 applies a third mode 2206 comprising three sub-modes 2214, 2216, 2218. In these modes, as illustrated, tissue impedance increases at a greater rate than in the second mode 2204 until a termination impedance (e.g., 500Ω) is reached.

In the embodiments described above, the electrosurgical drive signal (RF delivery) is terminated at the conclusion of the algorithm, typically at the conclusion of a tissue bite. To treat subsequent tissue bite, the clinician closes the jaws 164a, 164b over the subsequent tissue bite and then re-initiates the generator 120, 220 to provide the drive signal, for example, according to a delivery algorithm such as those described herein above with respect to FIGS. 9-18. In some embodiments, however, it is desirable for the surgical system 100, 200 to be maintained in an expert or repeat mode where provision of the drive signal is initiated for another tissue cycle automatically upon grasping a subsequent tissue bite and without the need for the clinician to manually toggle a button such as 128, 228. In an expert or speed mode of this type, the number of steps that a clinician must make to treat successive tissue bites is reduced as the clinician simply cycles the jaw closure control.

Figure 19:
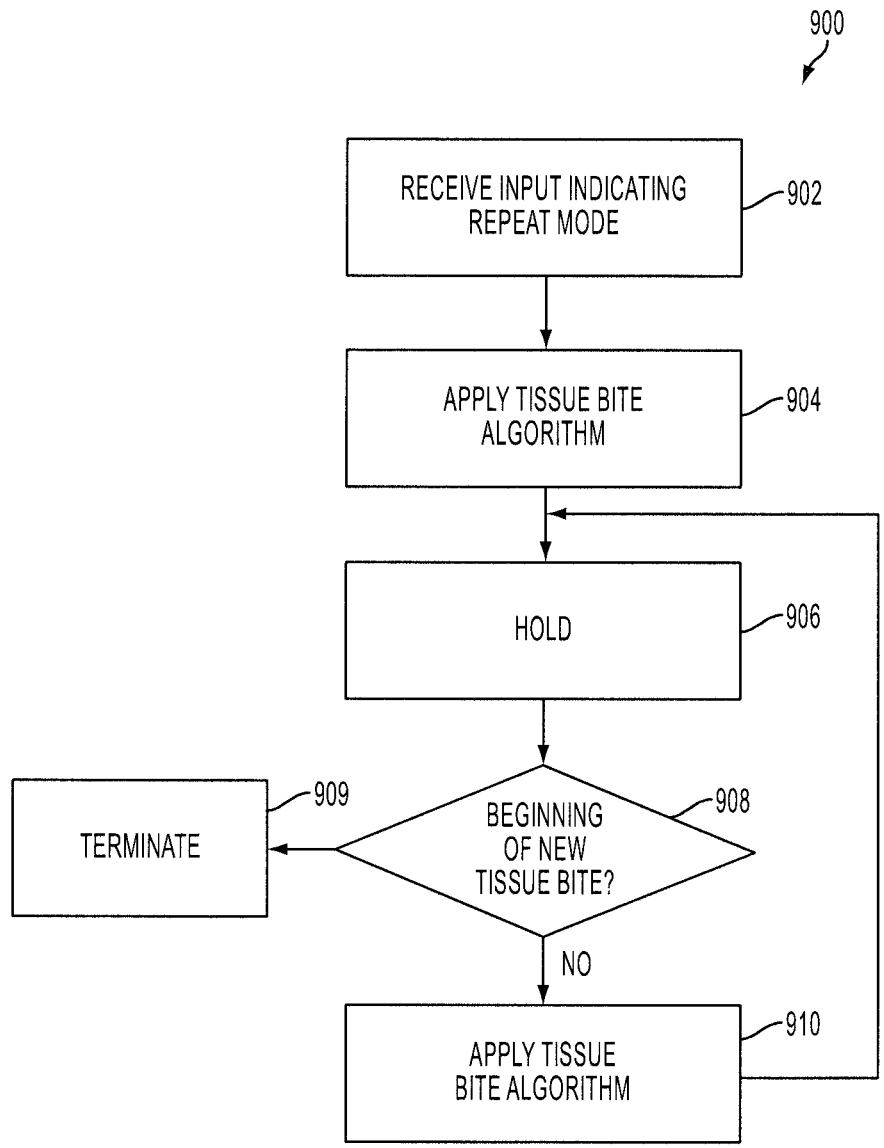
FIG. 19 shows one embodiment of a process flow for applying a repeat mode in the context of a surgical system such as those shown above in FIG. 1 and FIG. 7.

FIG. 19 shows one embodiment of a process flow 900 for applying a speed or expert mode in the context of a surgical system such as 100 or 200. At 902, the surgical system 100, 200 receives input from a clinician indicating the expert or repeat mode. The input of 902 may be received in any suitable manner. For example, in some embodiments, the clinician may indicate the expert or repeat mode by selecting the button 128, 228 twice as a "double-click." In some embodiments, the clinician invokes the expert or repeat mode by continuing to depress the button 128, 228 after the power delivery cycle or tissue bit algorithm has been completed. In some embodiments, the surgical systems 100, 200 may comprise an additional soft or hard input mechanism for indicating the repeat mode. For example, in some embodiments, the indication may be received via an input device 135 of the generator 120. At 904, the surgical system 100, 200 may apply a tissue bite algorithm. Any suitable tissue bite algorithm or power delivery algorithm may be used, including the algorithms 1330, 1452 described herein above utilizing power curves, as described. At the termination of the algorithm, the surgical systems 100, 200 may not terminate the drive signal, as described with respect to algorithms 1330, 1452. Instead, the surgical systems 100, 200 may enter a hold state 906. During the hold state, the generator 120, 220 may await an indication of the beginning of a new tissue bite. The drive signal may be terminated or maintained at a low level during the hold state. For example, in some embodiments, the drive signal may be maintained at a low level to facilitate the detection of a new tissue bite. For example, a sub-therapeutic output, such as a pulsed sub-therapeutic output, may be provided during the hold state 906. For example, the sub-therapeutic signal may facilitate the detection of a new tissue bite by allowing the system to continue to monitor the state of the end effector, as described herein below. In some embodiments, an end-of-cycle tone or other sound may be generated during the hold state. For example, the end-of-cycle tone or other sound may continue to loop while the clinician continues to hold the button 128, 228 closed. The continuation of audible feedback may serve as a reminder to the clinician that the system is still monitoring and awaiting a new tissue bite.

At 908, the electrosurgical system 100, 200 may determine whether a new tissue bite has begun. This may be determined in any suitable manner. For example, when the electrosurgical system 100, 200 maintains a sub-therapeutic drive signal during the hold state 906, the beginning of a new tissue bite may be determined by a reduction in impedance between the electrodes of the jaw members 164a, 164b. For example, when the jaw members 164a, 164b are in an open position without tissue between them, it may create the equivalent of an open circuit or near-open circuit, resulting in a large impedance. When the electrodes then contact a subsequent tissue bite, the impedance sensed by the sub-therapeutic signal is reduced. In some embodiments, the surgical system 100, 200 may detect an increase in impedance (indicating an opening of the jaws 164a, 164b) followed by a decrease in impedance (indicating closure of the jaws 164a, 164b on a new tissue bite). Impedance changes may be measured relative to any suitable reference including, for example, an impedance measured at the completion of the previous application or cycle of the tissue bite algorithm at 904. Any other suitable indicator of the beginning of a new tissue bite may be used. For example, in some embodiments, a new tissue bite may be indicated when the jaw-closure trigger 121, 221, is opened and then closed again.

When the beginning of a new tissue bite is detected at 908, the surgical system 100, 200 may apply another cycle of the tissue bite algorithm at 910. Upon completion of the cycle at 910, the electrosurgical system 100, 200 may again enter the hold state 906, as described herein. On the other hand, if no new tissue bite is detected at 908, the process 900 may terminate at 909. Termination of the output may include termination of the therapeutic as well as sub-therapeutic outputs, if any. The absence of a new tissue bite may be detected in any suitable manner. For example, if no new tissue bite is detected within a predetermined threshold time period after entering the hold state 906, termination 909 may result. In some embodiments, the threshold time period may be selected to be an integer multiple of the duration of the end-of-cycle tone. Also, for example, the handle 112, 212 may comprise an accelerometer or other suitable tilt sensor for sensing a position of the handle 112, 212. If the handle 112, 212 remains stationary for a predetermined amount of time, or is placed on a resting orientation, the surgical system 100, 200 may determine that no new tissue bite is detected and terminate at 909.

It will be appreciated that the process flow 900 may be implemented with different requirements for the actuation button 128, 228. For example, in some embodiments, the process flow 900 may terminate at 909 from any of the other actions when the clinician releases the actuation button 128, 228. In this way, the clinician may be provided with a way of ceasing the provision of energy. In other embodiments, it may not be necessary for the clinician to maintain actuation of the button 128, 228 in order to continue execution of the algorithm.

Figure 20:
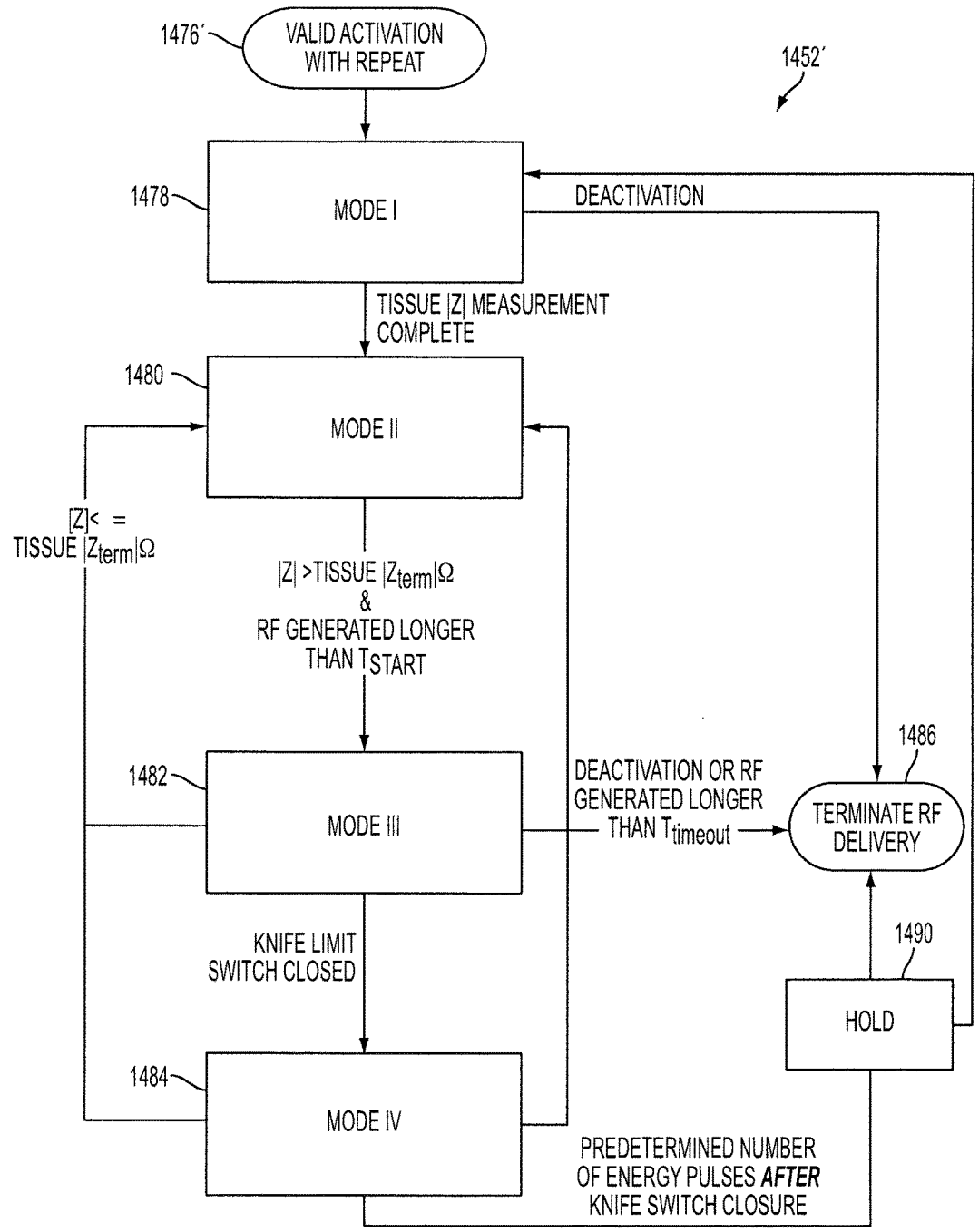
FIG. 20 shows an alternate embodiment of the process flow of FIG. 11 incorporating a repeat mode.
Figure 21:
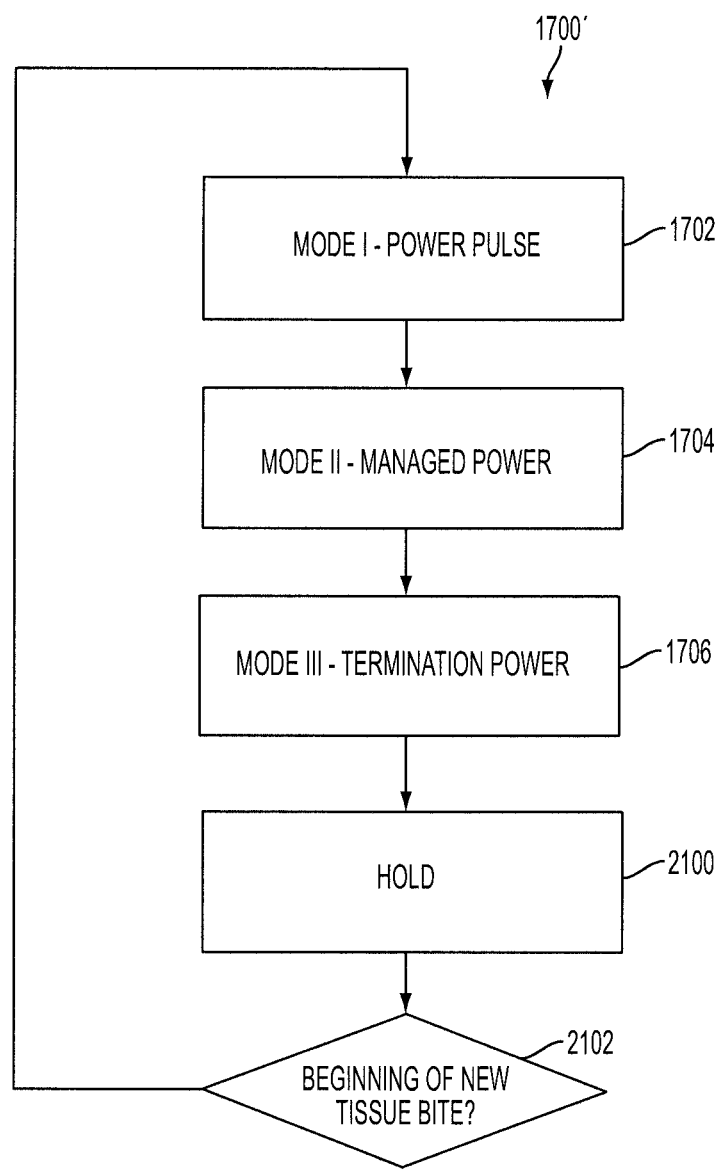
FIG. 21 shows an alternate embodiment of the process flow of FIG. 12 incorporating a repeat mode.

FIG. 20 shows an alternate embodiment of the process flow 1452' incorporating a repeat mode. The process flow 1452' may be activated at 1476'. Upon completion of the cycle at Mode IV (1484), the electrosurgical system 100, 200 may enter a hold mode 1490, similar to the hold mode 906. If the beginning of another tissue bite is detected at the hold mode 1490, the system may progress again to Mode I (1478). In various embodiments, the timeout time of the generator 120, 220 may not be reset upon re-entry of Mode I (1478). Other time-related thresholds related to the various modes 1478, 1480, 1482, 1484 may be reset. Also, tonal or other outputs from the systems 100, 200 may be reset so as to indicate to the clinician the mode in which the systems 100, 200 are operating. FIG. 21 shows an alternate embodiment of the process flow 1700' incorporating a repeat mode. Upon completion of the third mode 1706, the electrosurgical system 100, 200 may enter a hold mode 2100, similar to the hold mode 906. If the beginning of another tissue bite is detected at 2102, the system may progress again to the first mode (1702).

Although the embodiments described herein are electrosurgical systems, it will be appreciated that similar impedance management systems and methods may be utilized with any suitable type of surgical system including those that provide energy to tissue from an RF source, an ultrasonic source, a direct current source (e.g., a direct current source powering a heating element), etc. Surgical systems that do not provide current directly to the treated tissue may measure tissue impedance utilizing one or more sensor electrodes. Sensor electrodes may be positioned to contact the tissue. For example, in an ultrasonic surgical system, sensor electrodes may be embedded in a pad opposite an ultrasonic blade. The generator 120, 220 may be configured to provide a subtherapeutic electrical signal to the sensor electrodes. The resulting current and voltage drop may indicate tissue impedance. Example embodiments for implementing sensor electrodes and providing subtherapeutic signals are shown in U.S. Patent Application Publication No. 2011/0015627, entitled "Impedance Monitoring Apparatus, System and Method for Ultrasonic Surgical Instruments," which is incorporated herein by reference in its entirety.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

1. An electrosurgical system for providing an electrosurgical signal to a patient, the system comprising:
   a control circuit programmed to:
      for a first application period, apply the electrosurgical signal to first and second electrodes according to a first mode, wherein in the first mode, the control circuit limits the electrosurgical signal to a first maximum power when the impedance between the first and second electrodes exceeds a first mode threshold; and
      for a second application period after the first application period, apply the electrosurgical signal according to a second mode, wherein in the second mode, the control circuit limits the electrosurgical signal to a second mode maximum power when the impedance between the first and second electrodes exceeds a second mode threshold, wherein the second maximum power is greater than the first maximum power.
2. The electrosurgical system of clause 1, wherein the first mode threshold is less than the second mode threshold.
3. The electrosurgical system of clause 1, wherein the control circuit is further programmed to:

for a third application period after the second application period, apply the electrosurgical signal according to a third mode, wherein in the third mode, the control circuit limits the electrosurgical signal to a third maximum power when the impedance between the first and second electrodes exceeds a third mode threshold.

4. The electrosurgical system of clause 3, wherein in the third mode, the control circuit limits the electrosurgical signal to the third maximum power when the impedance between the first and second electrodes exceeds a third mode threshold during an application period of a first sub-mode, and wherein the control circuit is further programmed to:
for a fourth application period after the third application period, apply the electrosurgical signal according to a second sub-mode, wherein in the second sub-mode, the control circuit limits the electrosurgical signal to a fourth maximum power when the impedance between the first and second electrodes exceeds the third mode threshold, wherein the fourth maximum power is greater than the third maximum power.

5. The electrosurgical system of clause 4, wherein the control circuit is further programmed to:
for a fifth application period after the fourth application period, apply the electrosurgical signal according to a third sub-mode, wherein in the third sub-mode, the control circuit limits the electrosurgical signal to a fifth maximum power when the impedance between the first and second electrodes exceeds the third mode threshold, wherein the fifth maximum power is greater than the fourth maximum power.

6. The electrosurgical system of clause 3, wherein the control circuit is programmed to continue the third application period until the impedance between the first and second electrodes reaches a terminal threshold.

7. The electrosurgical system of clause 1, wherein the control circuit limits the electrosurgical signal to the first maximum power by limiting the electrosurgical signal to a first maximum voltage.

8. The electrosurgical system of clause 1, wherein in the first mode, the control circuit also limits the electrosurgical signal to a second first-mode maximum power when the impedance between the first and second electrodes exceeds a second first-mode threshold.

9. The electrosurgical system of clause 1, wherein the control circuit is further programmed to apply the electrosurgical signal during the first mode as a plurality of pulses.

10. The electrosurgical system of clause 1, wherein the control circuit is further programmed to:
after the first and second application periods, determine whether a new tissue bite has been initiated; and
upon determining that a new tissue bite has been initiated, apply the electrosurgical signal to the first and second electrodes according to the first mode.

11. A method for providing an electrosurgical signal to a patient using an electrosurgical system, the method comprising:
for a first application period, applying the electrosurgical signal to first and second electrodes of the electrosurgical system according to a first mode, wherein in the first mode, the electrosurgical signal is limited to a first maximum power when the impedance between the first and second electrodes exceeds a first mode threshold; and
for a second application period after the first application period, applying the electrosurgical signal according to a second mode, wherein in the second mode, the electrosurgical signal is limited to a second mode maximum power when the impedance between the first and second electrodes exceeds a second mode threshold, wherein the second maximum power is greater than the first maximum power.

12. The method of clause 11, wherein the first mode threshold is less than the second mode threshold.

13. The method of clause 11, further comprising:
for a third application period after the second application period, applying the electrosurgical signal according to a third mode, wherein in the third mode, the electrosurgical signal is limited to a third maximum power when the impedance between the first and second electrodes exceeds a third mode threshold.

14. The method of clause 13, wherein in the third mode, the electrosurgical signal is limited to the third maximum power when the impedance between the first and second electrodes exceeds a third mode threshold during an application period of a first sub-mode, and further comprising:
for a fourth application period after the third application period, applying the electrosurgical signal according to a second sub-mode, wherein in the second sub-mode, the electrosurgical signal is limited to a fourth maximum power when the impedance between the first and second electrodes exceeds the third mode threshold, wherein the fourth maximum power is greater than the third maximum power.

15. The method of clause 14, further comprising:
for a fifth application period after the fourth application period, applying the electrosurgical signal according to a third sub-mode, wherein in the third sub-mode, the electrosurgical signal is limited to a fifth maximum power when the impedance between the first and second electrodes exceeds the third mode threshold, wherein the fifth maximum power is greater than the fourth maximum power.

16. The method of clause 13, further comprising continuing the third application period until the impedance between the first and second electrodes reaches a terminal threshold.

17. The method of clause 11, wherein the electrosurgical signal is limited to the first maximum power by limiting the electrosurgical signal to a first maximum voltage.

18. The method of clause 11, wherein in the first mode, the electrosurgical signal is also limited to a second first-mode maximum power when the impedance between the first and second electrodes exceeds a second first-mode threshold.

19. The method of clause 11, further comprising applying the electrosurgical signal during the first mode as a plurality of pulses.

20. The method of clause 11, further comprising:
after the first and second application periods, determining whether a new tissue bite has been initiated; and
upon determining that a new tissue bite has been initiated, applying the electrosurgical signal to the first and second electrodes according to the first mode.

What is claimed is:
1. An electrosurgical system for providing an electrosurgical signal to a patient, the system comprising:

a control circuit programmed to:
  for a first application period during a coagulation cycle, apply the electrosurgical signal to first and second electrodes according to a first mode, wherein in the first mode, the control circuit is configured to:
    limit the electrosurgical signal to a first first-mode maximum power when an impedance between the first and second electrodes is less than a first mode threshold; and
    limit the electrosurgical signal to a second first-mode maximum power when the impedance between the first and second electrodes exceeds the first mode threshold, wherein the first first-mode maximum power is greater than the second first-mode maximum power; and
  for a second application period after the first application period during the coagulation cycle, apply the electrosurgical signal according to a second mode, wherein in the second mode, the control circuit is configured to:
    limit the electrosurgical signal to a first second-mode maximum power when the impedance between the first and second electrodes is less than a second mode threshold; and
    limit the electrosurgical signal to a second second-mode maximum power when the impedance between the first and second electrodes exceeds the second mode threshold, wherein the first second-mode maximum power is greater than the second second-mode maximum power,
  wherein the second second-mode maximum power is greater than the second first-mode maximum power.

2. The electrosurgical system of claim 1, wherein the first mode threshold is less than the second mode threshold.

3. The electrosurgical system of claim 1, wherein the control circuit is further programmed to:
  for a third application period after the second application period during the coagulation cycle, apply the electrosurgical signal according to a third mode, wherein in the third mode, the control circuit is configured to:
    limit the electrosurgical signal to a first third-mode maximum power when the impedance between the first and second electrodes is less than a third mode threshold; and
    limit the electrosurgical signal to a second third-mode maximum power when the impedance between the first and second electrodes exceeds the third mode threshold.

4. The electrosurgical system of claim 3, wherein in the third mode, the control circuit is configured to limit the electrosurgical signal to the second third-mode maximum power when the impedance between the first and second electrodes exceeds the third mode threshold during an application period of a first sub-mode, and wherein the control circuit is further programmed to:
  for a fourth application period after the third application period during the coagulation cycle, apply the electrosurgical signal according to a second sub-mode, wherein in the second sub-mode, the control circuit is configured to:
    limit the electrosurgical signal to a first second-sub-mode maximum power when the impedance between the first and second electrodes is less than the third mode threshold; and
    limit the electrosurgical signal to a second second-sub-mode maximum power when the impedance between the first and second electrodes exceeds the third mode threshold, wherein the second second-sub-mode maximum power is greater than the second third-mode maximum power.

5. The electrosurgical system of claim 4, wherein the control circuit is further programmed to:
  for a fifth application period after the fourth application period during the coagulation cycle, apply the electrosurgical signal according to a third sub-mode, wherein in the third sub-mode, the control circuit is configured to limit the electrosurgical signal to a third-sub-mode maximum power when the impedance between the first and second electrodes exceeds the third mode threshold, wherein the third-sub-mode maximum power is greater than the second second-sub-mode maximum power.

6. The electrosurgical system of claim 3, wherein the control circuit is programmed to continue the third application period until the impedance between the first and second electrodes reaches a terminal threshold.

7. The electrosurgical system of claim 1, wherein the control circuit is configured to limit the electrosurgical signal to the second first-mode maximum power by limiting the electrosurgical signal to a first maximum voltage.

8. The electrosurgical system of claim 1, wherein in the first mode, the control circuit is also configured to limit the electrosurgical signal to a third first-mode maximum power when the impedance between the first and second electrodes exceeds a second first-mode threshold.

9. The electrosurgical system of claim 1, wherein the control circuit is further programmed to apply the electrosurgical signal during the first mode as a plurality of pulses.

10. The electrosurgical system of claim 1, wherein the control circuit is further programmed to:
  after the first and second application periods, determine whether a new tissue bite has been initiated; and
  upon determining that a new tissue bite has been initiated, apply the electrosurgical signal to the first and second electrodes according to the first mode.

11. The electrosurgical system of claim 1, wherein the second application period is longer than the first application period.

12. The electrosurgical system of claim 11, wherein the first application period is about 1.4 seconds and the second application period is about 4 to 5.4 seconds.

* * * * *